United States Patent
Mazutis et al.

(10) Patent No.: US 12,360,024 B2
(45) Date of Patent: Jul. 15, 2025

(54) SYSTEMS AND METHODS FOR ENCAPSULATION AND MULTI-STEP PROCESSING OF BIOLOGICAL SAMPLES

(71) Applicants: Vilnius University, Vilnius (LT); Droplet Genomics, UAB, Vilnius (LT)

(72) Inventors: Linas Mazutis, Vilnius (LT); Greta Stonyte, Vilnius (LT); Karolis Leonavicius, Vilnius (LT); Ausra Zelvyte, Vilnius (LT)

(73) Assignees: Vilnius University, Vilnius (LT); Droplet Genomics, UAB, Vilnius (LT)

( * ) Notice: Subject to any disclaimer, the term of this patent is extended or adjusted under 35 U.S.C. 154(b) by 60 days.

(21) Appl. No.: 18/514,235

(22) Filed: Nov. 20, 2023

(65) Prior Publication Data

US 2024/0085287 A1    Mar. 14, 2024

Related U.S. Application Data

(62) Division of application No. 16/934,045, filed on Jul. 21, 2020, now Pat. No. 11,860,076.

(60) Provisional application No. 62/863,881, filed on Jun. 20, 2019.

(51) Int. Cl.
  *G01N 1/40* (2006.01)
  *B01J 13/04* (2006.01)
  *B01J 13/20* (2006.01)
  *C12Q 1/68* (2018.01)
  *C12Q 1/6806* (2018.01)

(52) U.S. Cl.
  CPC .......... *G01N 1/4077* (2013.01); *B01J 13/046* (2013.01); *B01J 13/206* (2013.01); *C12Q 1/6806* (2013.01)

(58) Field of Classification Search
  CPC ..... C12Q 1/6806; B01J 13/046; B01J 13/206; G01N 1/4077
  See application file for complete search history.

(56) References Cited

U.S. PATENT DOCUMENTS 5,084,350 A    2/1992  Chang
2017/0114390 A1*  4/2017  Hindson ............... C12Q 1/6869
2018/0362969 A1*  12/2018 Banal ................. C12N 15/1068

FOREIGN PATENT DOCUMENTS

WO    2019028166 A1    2/2019

OTHER PUBLICATIONS

Lan et al. Nature Biotechnology, Advance Online Publication May 29, 2017, pp. 1-7 (Year: 2017).*
Vijayakumar, K., Gulati, S., Demello, A. J. & Edel, J. B. Rapid cell extraction in aqueous two-phase microdroplet systems. Chem. Sci. 1, 447-452 (2010).
Tamminen, M. V. & Virta, M. P. J. Single gene-based distinction of individual microbial genomes from a mixed population of microbial cells. Front. Microbiol. 6, 1-10 (2015).
Ma, S. et al. Fabrication of microgel particles with complex shape via selective polymerization of aqueous two-phase systems. Small 8, 2356---2360 (2012).
Natanabe, Motohiro, and Ono, Microfluidic Formation of Hydrogel Microcapsules with a Single Aqueous Core by Spontaneous Crosslinking in Aqueous Two-Phase System (ATPS) Droplets. Langmuir, 2019.

* cited by examiner

*Primary Examiner* — Jezia Riley
(74) *Attorney, Agent, or Firm* — Garrett H. Anderson

(57) ABSTRACT

This invention relates to methods and systems for isolation of species in semi-permeable capsules and processing of encapsulated species through series of steps and/or reactions. To produce capsules, first aqueous two-phase system (ATPS) droplets are generated using microfluidics system. Then the hydrogel shell layer is hardened by inducing polymerization. As exemplified in this invention to achieve concentric ATPS droplet formation density-matched PEGDA and Dextran polymer solutions can be used. Once a capsule is formed, its composition can be changed by adding new reagents or replacing out old ones (e.g. by resuspending capsules in desired aqueous solution). The hydrogel shell of semi-permeable capsules can be dissolved at selected step during multi-step procedures to release the encapsulated species. This invention exemplifies isolation of individual cells within capsules and using the encapsulated cells for genotypic and phenotypic analysis. This invention also exemplifies use of capsules in multi-step procedures to perform complex biological reactions.

20 Claims, 12 Drawing Sheets

SYSTEMS AND METHODS FOR ENCAPSULATION AND MULTI-STEP PROCESSING OF BIOLOGICAL SAMPLES

CROSS REFERNECES

This is a divisional application of U.S. application Ser. No. 16/934,045 filed on Jul. 21, 2020 and claiming priority of U.S. provisional application 62/863,881 filed on Jun. 20, 2019.

FIELD OF THE INVENTION

The present invention is directed to methods and systems for isolation of species such as cells, bacteria, viruses, nucleic acids, biochemical compounds, and/or other materials in semi-permeable capsules, and processing the encapsulated species through multi-step procedures to perform sequential reactions. The encapsulated species can be released from capsules at a desirable step upon treatment with a specific agent or external stimuli. The method revealed here exemplifies the use of capsules for genotypic and phenotypic analysis of individual cells.

BACKGROUND OF THE INVENTION

High-throughput processing and analysis of biological samples at the single-cell or single-molecule resolution has important applications in many branches of life sciences. Compartmentalization of cells, DNA, enzymes or molecules to water-in-oil droplets or other forms of compartments enables massively parallel analysis with a throughput orders of magnitude higher when compared to 96-well microtiter plates. However, many molecular biology methods are built on sequential and multi-step sample processing in order to initiate, modify or terminate a reaction. As a result, not all molecular biology workflows can be easily transferred to droplet or other types of emulsion-based formats. Although some solutions such as droplet fusion, reinjection, and splitting can enable multi-step procedures (e.g. to add new reagents to a preformed droplet), yet the required expertise and complexity of fluidic operations limits the broader use of such approaches. Sequential sample processing can become very challenging when encapsulated cells, or their genetic material, have to be processed through a series of independent reactions. For example, for the amplification and/or analysis of genetic material of encapsulated cells it may be necessary to perform cell lysis, a step that might be inhibitory or detrimental to subsequent enzymatic step(s). As a result, it is advantageous to have a method and/or system that would enable buffer/reagent exchange and/or removal of lysis reagents, before nuclei acid analysis/amplification step. Considering current state-of-the-art there is unmet need for methods and systems that would enable multi-step processing of encapsulated entities (e.g. cells). The invention revealed here is related to production of capsules with semi-permeable hydrogel shell and use of the said capsules for processing biological samples, as exemplified by performing genotypic and phenotypic analysis on individual cells.

Previous attempts to produce capsules suitable for multi-step biological reactions have not been successful or practical. Although numerous reports have shown generation of semi-permeable capsules composed of variety of polymers, yet to the best of our knowledge no capsules have been shown or applied in multi-step reactions to process of, or perform analysis on, encapsulated entities such as cells, biomolecules, etc.

For example, Vijayakumar, K., Gulati, S., Demello, A. J. & Edel, J. B. *Rapid cell extraction in aqueous two-phase microdroplet systems. Chem. Sci.* 1, 447-452 (2010) applied droplet microfluidic system to generate an aqueous two-phase system (ATPS) in which aqueous droplets consist of two phases: PEG-rich and Dextran-rich. They demonstrated T lymphoma cell partitioning between two layers. However, the authors have not produced semi-permeable capsules.

Tamminen, M. V. & Virta, M. P. J. *Single gene-based distinction of individual microbial genomes from a mixed population of microbial cells. Front. Microbiol.* 6, 1-10 (2015). The method of generating capsules is significantly different from the one described in this invention. In this work bacteria are encapsulated to acrylamide hydrogel beads, then the beads carrying embedded bacteria are resuspended in warm agarose and emulsified again that leads to capsules with a hydrogel core composed of acrylamide and hydrogel-shell composed of agarose. The authors show that the hydrogel core can be dissolved by DTT, as a result forming liquid core capsules with agarose shell. The method and system revealed here involves different steps and generation of capsules relies on microfluidic systems.

Ma, S. et al. *Fabrication of microgel particles with complex shape via selective polymerization of aqueous two-phase systems. Small* 8, 2356-2360 (2012). Although the authors have used similar polymers, Dextran and PEGDA to produce aqueous two-phase system (ATPS) droplets they presented a method for fabricating micro particles with a concave shape. In one aspect, the invention comprises a method for producing capsules but the biological samples cannot be contained in such open particles.

Watanabe, Motohiro, and Ono, *Microfluidic Formation of Hydrogel Microcapsules with a Single Aqueous Core by Spontaneous Crosslinking in Aqueous Two-Phase System (ATPS) Droplets. Langmuir,* 2019. The authors have demonstrated the fabrication of monodisperse tetra-arm poly (ethylene glycol) (tetra-PEG) hydrogel microcapsules with an aqueous core and a semi-permeable hydrogel shell through the formation of aqueous two-phase system (ATPS) droplets consisting of Dextran (DEX)-rich core and tetra-PEG macromonomer-rich shell, followed by spontaneous cross-end coupling reaction of tetra-PEG macromonomers in the shell. The workflow of capsule generation has similarities with the methods and systems reported here. However, the authors have not shown any of the biological applications such as analysis and processing of cells or biological samples, or the possibility of using capsules for multi-step reactions.

In the following sections the invention reveals a few, but not limited to, examples of semi-permeable capsule production, encapsulation of species (such as cells), the use encapsulated-species in multi-step processes and sequential reactions, genotypic and phenotypic analysis of individual cells in a massively parallel fashion and other applications.

SUMMARY OF THE INVENTION

The present invention is directed to systems and methods for production of semi-permeable capsules, the capsule use for encapsulation of cells and other biological materials, and for high-throughput processing of encapsulated material in multi-step operations. To form the capsules, first the liquid droplets are generated using microfluidics platform, then liquid-liquid phase separation is allowed to occur in droplets to form so called aqueous two-phase system (ATPS) droplets, then the shell of capsules is hardened by inducing polymerization of one of the phases of the ATPS droplet. As revealed in this invention, the capsule may consist of Dextran-rich solution that forms a capsule's core, and polyethylene glycol diacrylate (PEGDA) polymer-based shell. However, other combinations and polymers are also possible to use as should be evident from the capsules production steps revealed here. To exemplify the formation of the shell in ATPS droplets we use photo-illumination, as a chemically neutral measure to induce PEGDA polymerization and form hardened shell. Resulting capsules contain liquid-like core enriched in Dextran phase and hydrogel-shell enriched in PEGDA. The core of capsules can become more viscous after polymerization due to the presence of residual PEGDA and/or in some cases may form a hydrogel mesh. As revealed here the resulting capsules can be used in multi-step reactions to process cells and/or various biological materials (e.g. enzymes, proteins, viruses, nucleic acids, etc.). For example, the capsules can be used to isolate individual cells, to amplify the nucleic acids of encapsulated cells and perform other reactions required for genotypic analysis. In yet another example, capsules can be used for growing cells in capsules to perform phenotypic or genotypic screens and analysis. As shown here, single-cells can be expanded into micro-colonies. In all these analyses and operations, the ability to perform multi-step reactions on many capsules at once is an essential part of this invention. When suspended and washed in aqueous buffer multiple times the capsules are stiff enough to withstand mechanical stress and remain highly uniform. As revealed here the semi-permeable capsules can be used to perform genotypic and phenotypic analysis of individual bacterial cells in a massively parallel fashion. Furthermore, capsules sustained multiple temperature cycles during PCR as well as share forces generated during flow cytometry. Therefore, the invention is related to the use of semi-permeable capsules to isolate cells and/or biological material and samples for further multi-step processing and/or analysis.

In one aspect, the invention comprises a method for forming/providing a fluidic droplet containing the species, causing a separation into inner and outer phases of the fluidic droplet containing the species, inducing the gelation of the outer phase of the fluidic droplet containing the species, and performing multi-step reaction(s) and/or processing on the encapsulated species.

The "species" herein refers to cells, bacteria, viruses, DNA, RNA, proteins, biological material or biochemical compounds that will be processed in multi-step reaction.

In one exemplary embodiment, the invention comprises a microfluidic system for the production of liquid droplets containing the species. Such system comprises:
 (i) An inlet for continuous phase (carrier oil);
 (ii) An inlet for the first fluid;
 (iii) An inlet for the second fluid;
 (iv) A nozzle or a flow-focusing junction where droplet formation occurs;
 (v) A droplet collection outlet.
 (vi) Channel connecting the nozzle with the collection outlet.
 (vii) The species are provided with first fluid, with second fluid or with both.

In another aspect, the invention comprises the method for the formation of liquid droplets containing the species:
 (i) Injection of a first fluid (Phase I solution);
 (ii) Injection of a second fluid (Phase II solution);
 (iii) Injection of a carrier oil;
 (iv) Bringing carrier oil, Phase I and Phase II solutions to a flow-focusing junction;
 (v) Encapsulation of Phase I and Phase II in droplets suspended in carrier oil;
 (vi) Droplet collection off-chip.
 (vii) The species are provided with first fluid, with second fluid or with both.

The term "Phase I solution", as used herein, refers to a solution that is miscible with Phase II solution, but it can form a separate phase during so called liquid-liquid phase separation process, which occurs passively or upon external force (e.g. gravity). Similarly, the term "Phase II solution", as used herein, refers to a solution that is miscible with Phase I solution, but can form a separate phase during liquid-liquid phase separation process.

In one aspect, Phase I solution is rich in Dextran.

In another aspect, Phase II solution is rich in a polymer based on polyethylene glycol.

In one exemplary embodiment, the droplet generation occurs at cross-junction having a nozzle (constriction) where the break-up of fluid stream into monodisperse droplets occurs.

In another aspect, the invention comprises the method in which the phase separation of Phase I and Phase II solutions occurs in liquid droplets.

In another aspect, the invention comprises the method in which the Phase I and Phase II solutions form inner phase and outer phase in liquid droplets.

In yet another aspect, the invention comprises the method in which the Phase II is hardened by triggering a polymerization.

(Polymerization (gelation) herein, refers to the process in which a liquid form of "Phase II solution" is forming a solid or semi-sold hydrogel in the contact with "inducer". Typically, but not limited to, inducer can be light, chemical compounds, temperature, etc.

In yet another aspect, the invention comprises the method in which capsules are released from droplets by breaking the emulsion.

In yet another aspect, the invention comprises the capsules composed of semi-permeable shell and liquid-like core.

In one exemplary embodiment, the cells, biochemical and biological compounds are introduced in droplets by supplying them:
 (i) In the "Phase I solution";
 (ii) In the "Phase II solution";
 (iii) In all solutions.

In one aspect the invention describes the use of capsules for processing encapsulated species in multi-step sequential operations.

In another aspect the invention describes the use of capsules for performing multi-step reactions on encapsulated species.

In another exemplary embodiment, encapsulated species are cells that are lysed inside the capsules.

In another exemplary embodiment, the reagents that were used to lyse the cells are replaced by suspending capsules in a different buffer.

In yet another exemplary embodiment, the buffer in which cells were lysed is replaced with another buffer by suspending capsules in a said buffer.

In one exemplary embodiment, the encapsulated species are processed in multi-step sequential operations to perform a desirable biochemical or biological reaction.

In one exemplary embodiment, said reaction can be DNA amplification where the nuclei acids of lysed cells are amplified enzymatically using phi29 DNA polymerase.

In another exemplary embodiment, the nuclei acids of lysed cells are amplified enzymatically by PCR.

In another exemplary embodiment, the encapsulated cells are maintained alive over extended periods of time.

In another exemplary embodiment, the encapsulated cells are cultivated over extended periods of time.

In another specific embodiment, the individual cells are expanded into microcolonies.

In one specific exemplary embodiment, the encapsulated cells are screened for biological activity (e.g. production of metabolites, proteins, compounds, etc.)

In another exemplary embodiment, the phenotypic and/or genotypic analysis is performed on encapsulated cells and/or their material.

In one exemplary embodiment, the above methods are carried out but not limited to using a microfluidics system.

In one exemplary embodiment, the capsules have a size ranging from approximately 20 to 100 μm.

Figure 13:
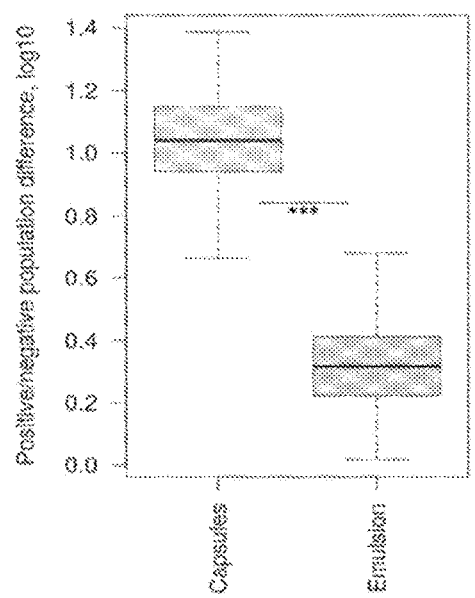

FIG. 13. Normalized fluorescence of positive droplets and capsules containing E. coli colonies after 4 hours growth. Boxplots are derived from samples of N>500 measurements, stars show statistical significance based on t-test.

Figure 14:
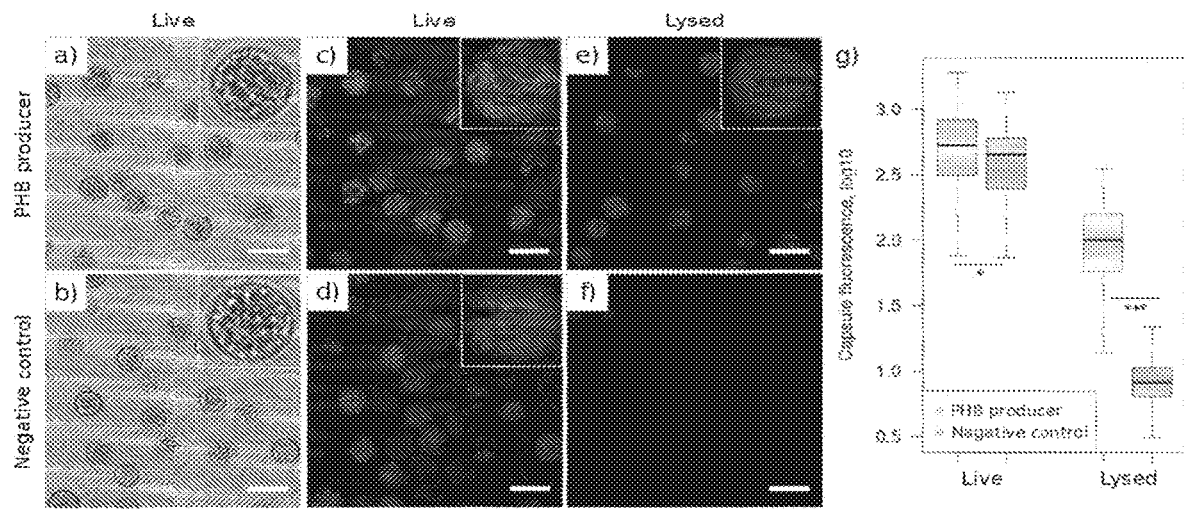

FIG. 14. Phenotypic analysis of PHB-producing micro-colonies based on Nile Red staining. Live micro-colonies of bacteria producing PHB (a and c) and negative control (b and d) showing no significant difference in fluorescence. Lysed micro-colonies of PHB-producing clones (e) and negative control (f) after washing the capsules to remove solubilized membranes. (g) Boxplot showing how cell lysis and capsule washing increased the ability to resolve PHB-producing colonies from negative controls. Exposure times for (c)-(f) images were 100 ms. Boxplots are derived from samples of N>100 measurements, stars show statistical significance based on t-test. Scale bars, 50 µm.

Figure 15:
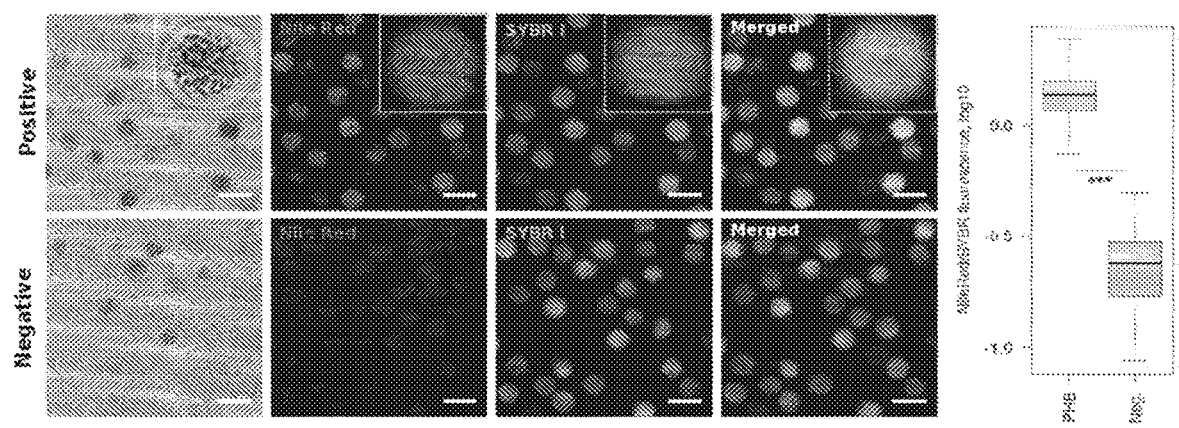

FIG. 15. Evaluation of bacterial metabolite PHB synthesis following single-cell derived colony expansion and lysis. Left: capsules with positive (DH5α-pBHR68) and negative (DH5α-pTZ18R) bacteria. Bright field images show lysed micro-colonies, Nile Red staining shows PHB metabolite amount, SYBR I indicates bacteria quantity in individual capsules based on gDNA staining, and Merged image shows Nile Red and SYBR I images combined. Lysed bacteria were stained with Nile Red and SYBR Green I to normalize PHB levels to bacteria count. Scale bars, 50 µm. Right: boxplots are derived from samples of N>100 measurements, stars show statistical significance based on t-test.

Figure 16:
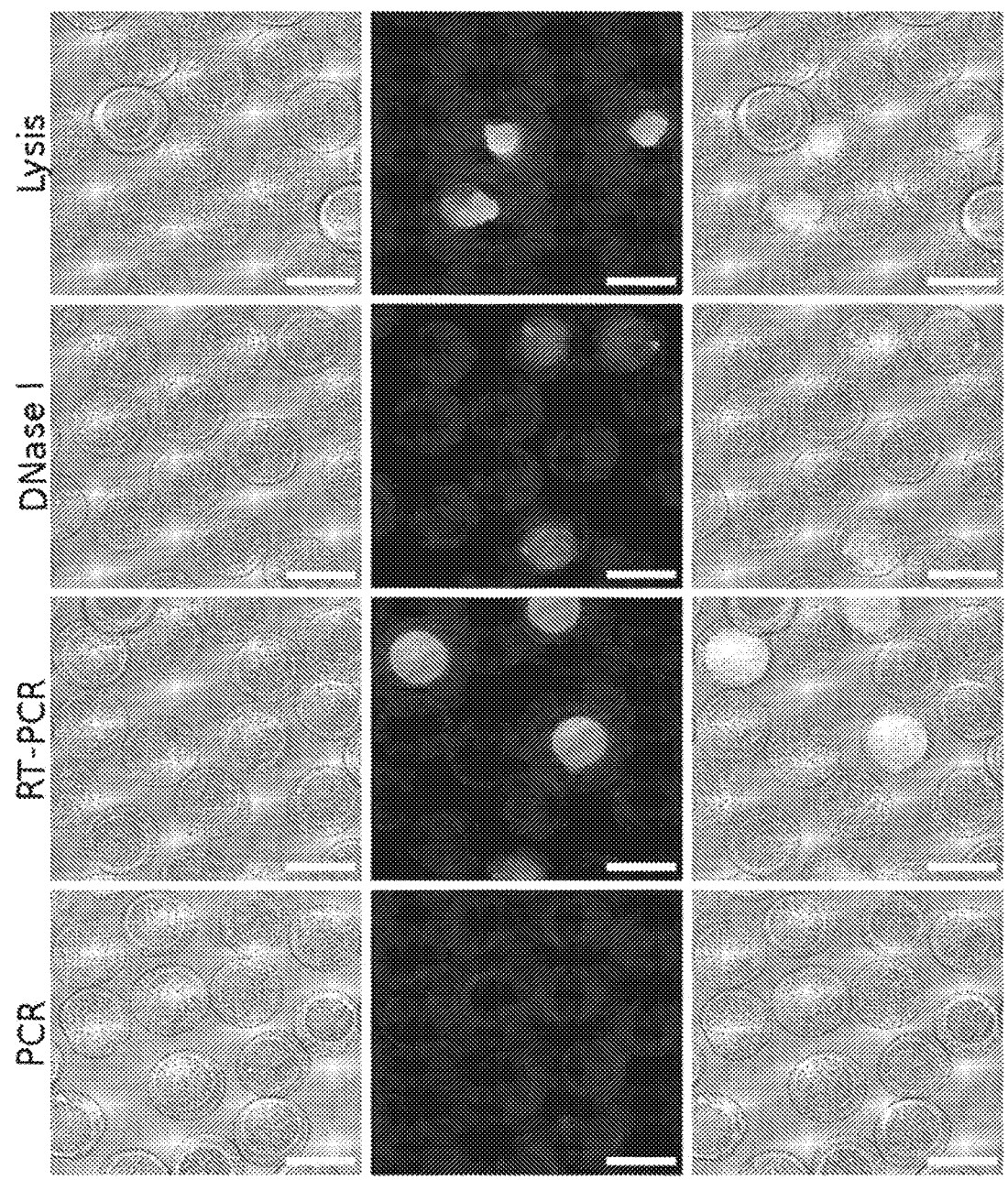

FIG. 16. Evaluation of reverse transcription and PCR reaction on mammalian cells using capsules. Bright-field and fluorescence microscopy, and merged images of mammalian cells in capsules after lysis, DNAse I treatment, RT-PCR and PCR (without RT) are shown. Samples were stained with SYBR Green I dye. Scale bars, 100 µm.

Figure 17:
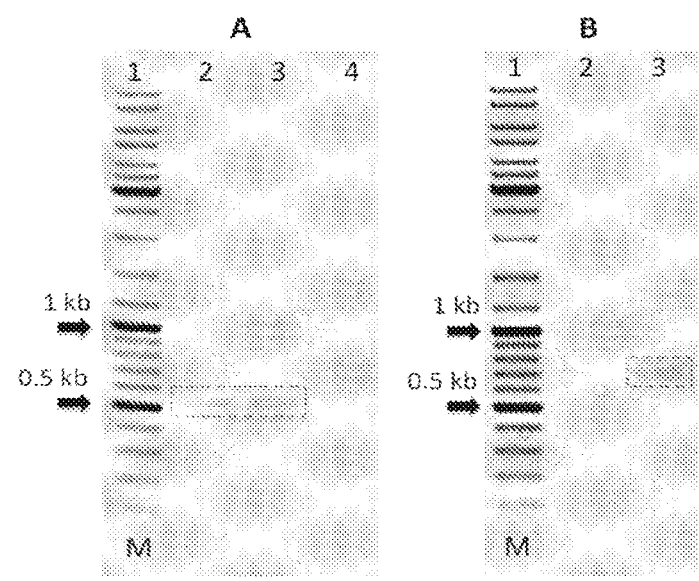

FIG. 17. DNA recovery and analysis of PCR and RT-PCR product formation on capsule-encapsulated mammalian cells. The results in „A" gel were obtained performing cell lysis, while the results in „B" gel—applying both cell lysis and gDNA elimination steps before PCR and RT-(PCR), respectively.

A gel:
 Well-1, M—GeneRuler DNA Ladder Mix (SM0331);
 Well-2, SRSF1 amplicon obtained by performing PCR;
 Well-3, SRSF1 amplicon obtained by performing PCR;
 Well-4, Negative control: –PCR enzyme using the same capsules as above.

B gel:
 Well-1, M—GeneRuler DNA Ladder Mix (SM0331);
 Well-2, Negative control: no RT step (only PCR) using the same capsules as in 3th sample;
 Well-3, ACTB amplicon obtained by performing RT-PCR.

SRSF1 product (~500 bp) and ACTB product (~700 bp), marked with red and green squares, respectively, were obtained after DNA extraction from ~10 µL close-packaged capsules. M—GeneRuler DNA Ladder Mix (SM0331).

Figure 18:
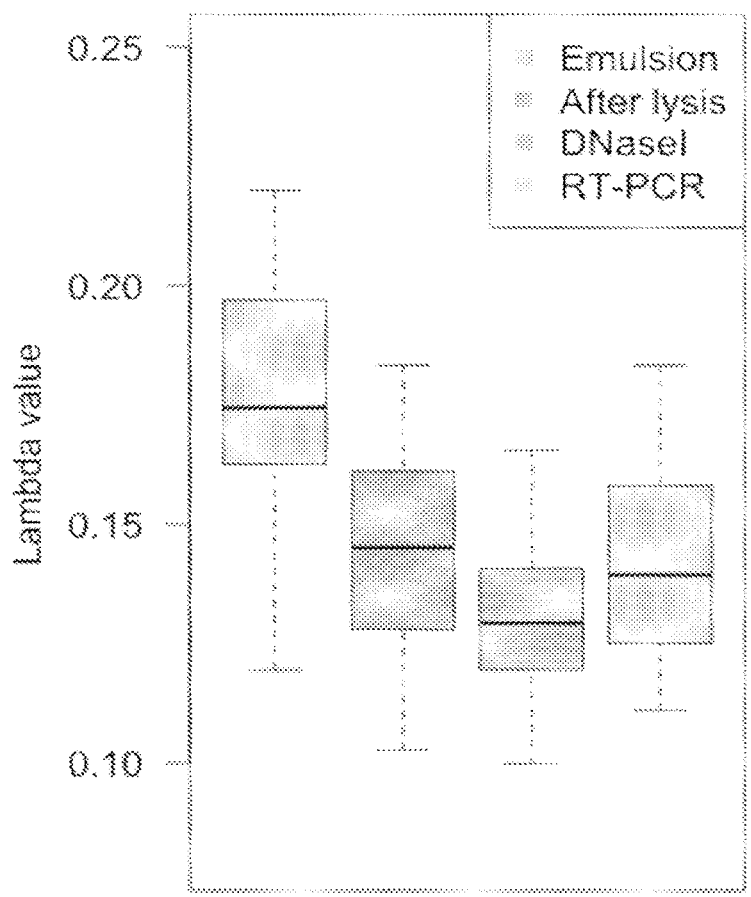

FIG. 18. Occupancy (lambda value) measurements at different stages of encapsulated cell processing. Green, blue, red and orange boxplots show lambda value in water-in-oil droplets, in capsules after lysis, in capsules after DNAse I treatment and in capsules after RT-PCR.

Figure 19:
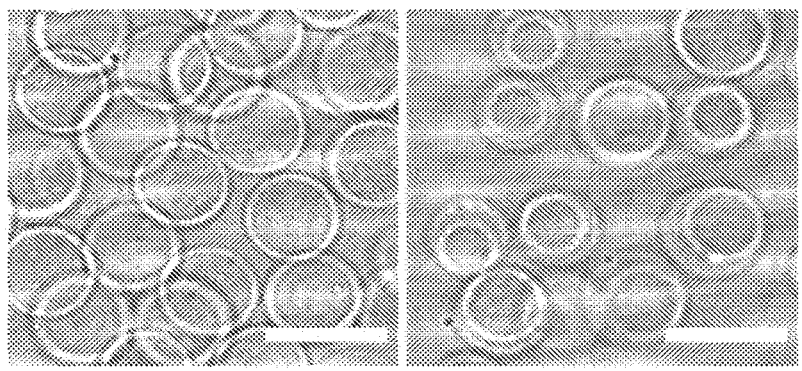

FIG. 19. Other examples of semi-permeable capsules. Left: capsules produced using PEGDA-Citrate system. Right: capsules produced using PEGDA-PVA system. Scale bars, 50 µm.

Figure 20:
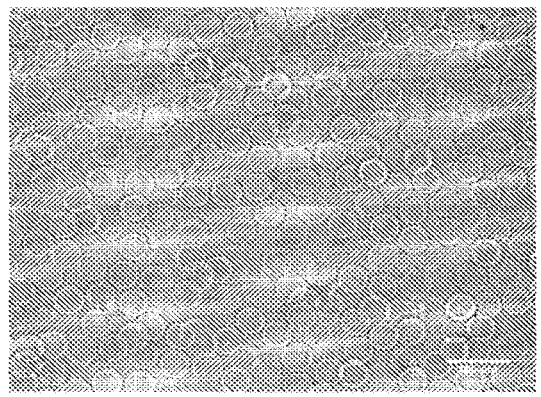

FIG. 20. Example of hydrogel capsules whose shell can be dissolved with reducing agents such as 10 mM DTT. Scale bar, 100 µm.

Figure 21:
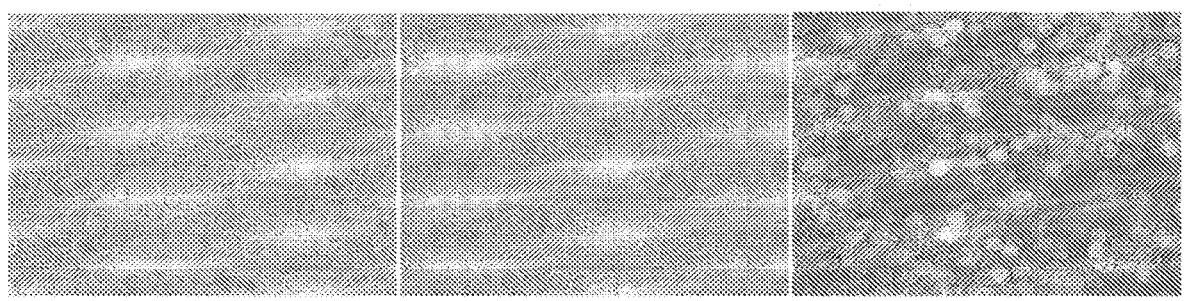

FIG. 21. Example of hydrogel capsules (whose shell can be dissolved with reducing agents) use to perform multi-step operations and reactions on encapsulated species. Capsules before E. coli lysis (the left picture), after E. coli lysis (the middle picture) and capsules after PCR with kdsC primers being used (the right picture).

Figure 22:
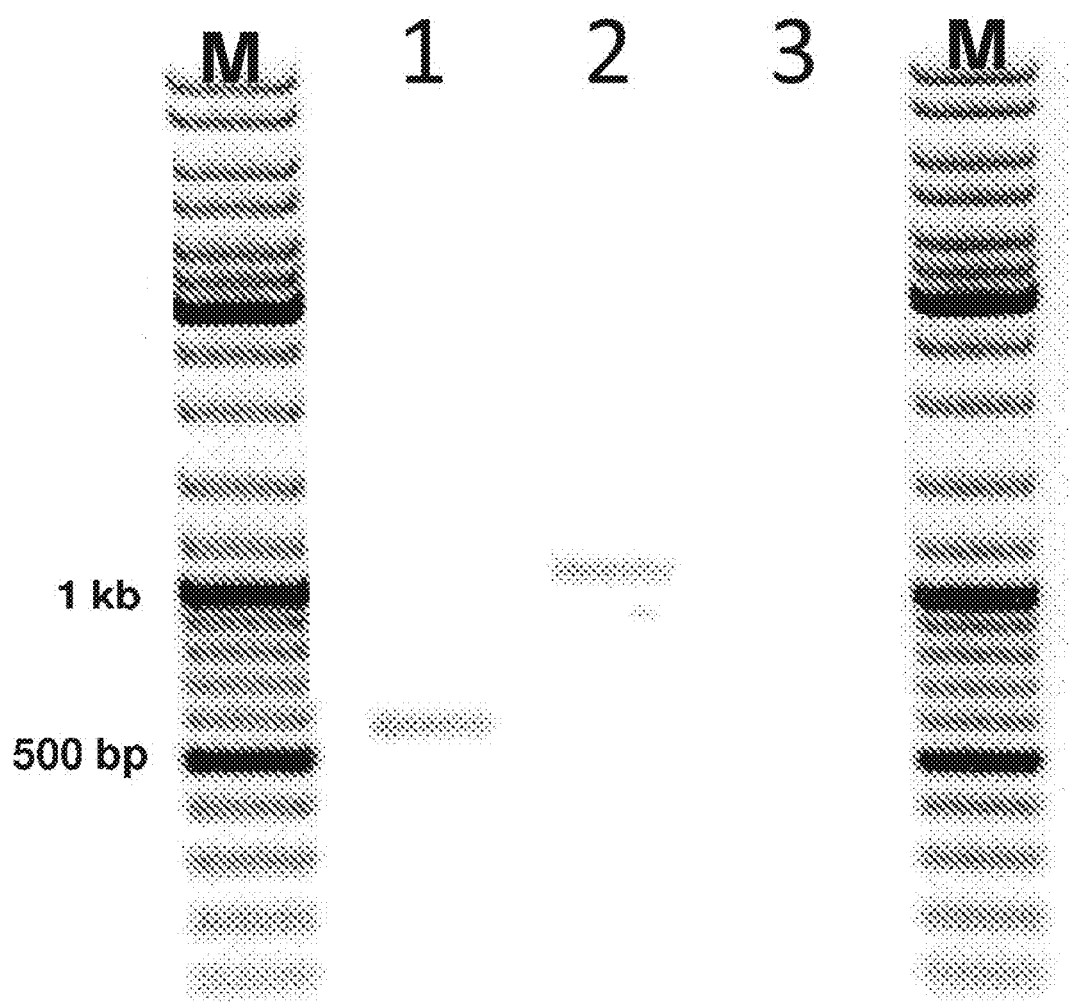

FIG. 22. Agarose gel of PCR product released from capsules. M—GeneLuler DNA ladder Mix. Lane 1—PCR product using kdsC primers, Lane 2—PCR product using ompA primers and Lane 3—negative control.

DETAILED DESCRIPTION OF THE INVENTION

The present invention generally relates to multi-step processing of capsule-encapsulated species to perform desired biological or biochemical reaction(s). In this context the capsules provide the semi-permeable compartment (reactor) for processing encapsulated species through multiple chemical conditions. The capsules may be used for encapsulation of cells, viruses, DNA and/or other biological compounds. In some cases, the capsules may be used in biological or biochemical assays. In some other cases, the present invention relates to alternative solutions to a particular problem, and/or a plurality of different uses of one or more systems and/or methods.

In one aspect the invention is a method for multi-step processing of capsule-encapsulated species. The present invention provides a method for forming/providing a fluidic droplet containing the species, causing a separation into inner and outer phases of the fluidic droplet containing the species, inducing the gelation of the outer phase of the fluidic droplet containing the species, and performing reaction(s) and/or analysis on the encapsulated species.

In another aspect the invention is a method for encapsulation of biochemical and biological compounds, cells, viruses, DNA and other molecules to perform desired biochemical or biological reaction on encapsulated species. Once the capsule is formed and species are isolated, the composition of the capsules can be changed by adding new reagents or replacing out old ones (e.g. by capsule resuspension in desired solution).

In another aspect the invention is a method for performing multi-step operations on encapsulated entities. The encapsulated entities (e.g. cells, DNA, etc) can be retained inside the capsules or released from them upon external stimulus as deem desirable.

In the method of the invention, the encapsulated species are exposed to different chemical conditions in a sequential manner in order to perform a desirable reaction on encapsulated species.

In the method of the invention, the microfluidics chip comprises, but not limited to, following units:
 (i) an inlet and microfluidic channel(s) for carrier oil;
 (ii) an inlet and microfluidic channel(s) for the first fluid;
 (iii) an inlet and microfluidic channel(s) for the second fluid;
 (iv) a nozzle or cross-junction;
 (v) a microfluidics channel connecting the nozzle with the outlet, and
 (vi) collection outlet.

In another aspect, the invention comprises the method for the formation of liquid/fluid droplets using microfluidics chip for:
(i) Injection of a "Phase I solution";
(ii) Injection of an "Phase II solution";
(iii) Injection of a carrier oil;
(iv) Brining carrier oil, Phase I and Phase II solutions to a flow-focusing junction;
(v) Encapsulation of Phase I and Phase II solutions in droplets suspended in carrier oil;
(vi) Droplet collection off-chip.

The term "microfluidic chip", as used herein, refers to a device, or chip, of only millimetres to a few square centimetres or tens of centimetres in size dealing with the handling of extremely small fluid volumes down to less than picoliters. Microfluidic chips are usually fabricated by using lithography-based technologies such as soft lithography.

In an embodiment, the fluids are introduced into the microfluidics chip via an inlet(s) and pass through the passive filter(s) and/or fluid resistor(s).

In a more particular embodiment, passive filters used in the chip of the invention are used to prevent microfluidic channels from clogging and act as solid support to avoid collapse of device structure. The fluid resistors damp fluctuation that might arise during device operation. These units may be well-known by the skilled person and their uses are illustrated in FIG. 1.

Figure 1:
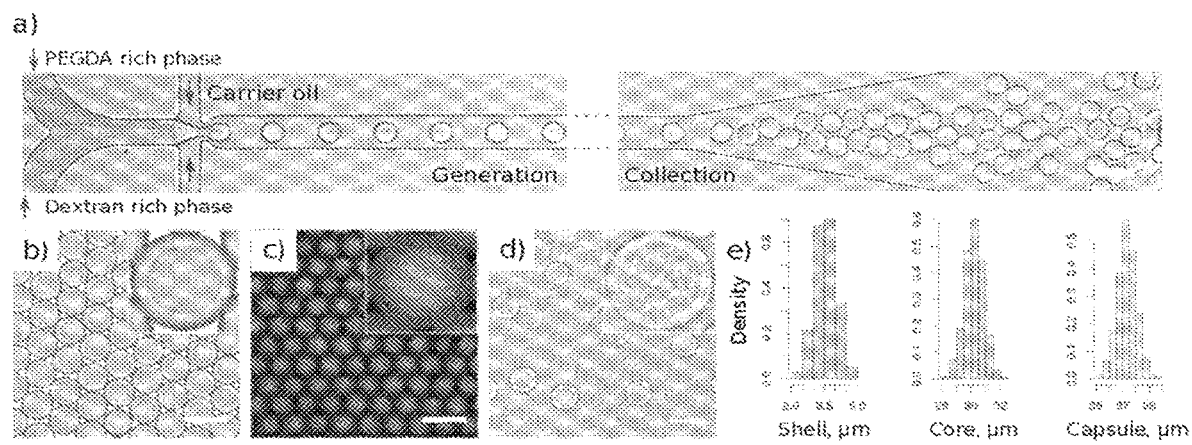
FIG. 1: Concentric capsule production and characterization. (a) Capsule formation using co-flow microfluidic device. (b) Liquid-liquid phase separation inside double emulsion droplets resulting in Dextran-rich core and PEGDA-rich shell. (c) Double emulsion droplets from panel (b) imaged under fluorescence microscope. Droplets contained 0.1% (w/v) fluorescein isothiocyanate-Dextran (MW 500K). (d) Capsules recovered from emulsion, where PEGDA shell formed firm hydrogel and Dextran phase formed liquid-like core. (e) Histograms, derived from N>100 measurements, indicate capsule shell thickness, capsule core and overall diameter. Scale bars, 50 μm.

In an embodiment, the micro-channels of each fluid are merging into a single micro-channel upstream the flow-focusing junction where individual fluids meet but do not mix (FIG. 1).

In an embodiment, the depth of the microfluidic channels are in the range from 1 µm to 100 µm, preferably in the range 10-40 µm.

In the method of the invention, the droplet generation occurs at cross-junction having a nozzle (constriction) where the break-up of fluid stream into monodisperse droplets occurs.

In the method of the invention, the Phase I and Phase II solutions are injected to microfluidics chip and form fluid droplets.

The term "Phase I", as used herein, refers to a solution that is miscible with Phase II solution, but it can form a separate phase during so called liquid-liquid phase separation process, which occurs passively or upon external force (e.g. gravity). Similarly, the term "Phase II", as used herein, refers to a solution that is miscible with Phase I solution, but can form a separate phase during liquid-liquid phase separation process.

In an embodiment, Phase I solution is rich in Dextran.

In an embodiment, Phase II solution is rich in modified polyethylene glycol polymer that can be cross-linked.

In another aspect, the phase separation occurs in droplets (FIG. 1).

In another aspect or the invention comprises the Phase I and Phase II solutions form inner phase and outer phase in liquid droplets, respectively.

In the method of the invention, the Phase I and Phase II solutions can be selected from a range of polymer systems available, as described in J. M. S. Cabral, *Cell Partitioning in Aqueous Two-Phase Polymer Systems*, Adv Biochem Engin/Biotechnol (2007).

In the method of the invention, the Phase II solution is hardened by inducing a polymerization (e.g. using light). Polymerization (gelation) herein, refers to the process in which a liquid form of "Phase II solution" is forming a solid or semi-sold hydrogel in the contact with "inducer". Typically, but not limited to, inducer can be light, chemical compounds, temperature, etc.

In the method of the invention, once the capsule is formed its composition can be changed by adding new reagents or replacing out old ones.

In the method of the invention, the liquid droplets are collected off-chip via outlet.

In an embodiment, the droplets are generated on the microfluidic chip comprising a flow-focusing junction (as illustrated in FIG. 1) allowing the production of droplets of different size. The droplet size can be controlled by adjusting the flow rates of Phase I and Phase solutions and carrier oil and/or the cross-section of a nozzle and/or the cross-section of microfluidics channels.

In an embodiment, the droplets are generated at a frequency ranging from 0.01 Hz to 10 kHz, preferably from 0.1 kHz to 5 kHz, more preferably from 0.5 kHz to 2.5 kHz. A frequency of 1 kHz means that droplets are provided at a rate of 1000 droplets per second.

As used in this specification, the term "about" refers to a range of values ±10% of the specified value. For example, "about 20" includes ±10% of 20, or from 18 to 22. Preferably, the term "about" refers to a range of values ±5% of the specified value.

In an embodiment, the droplets have a volume ranging from 0.01 pL to 1000 nL, preferably from 100 pL to 500 pL and more preferably from 10 pL to 100 pL.

In a particular embodiment, Phase I, Phase II or both solutions may comprise, for instance, various chemical compounds such as buffers, salts, carbohydrates, lipids, polymers, proteins, nucleic acids, cells or micro-organisms.

In a particular embodiment, the carrier oil used to generate droplets is a fluorinated oil and comprises a surfactant, a PFPE-PEG-PFPE (perfluoropolyether-polyethylene glycol-perfluoropolyether) tri-block copolymer. Said surfactant being present in the carrier oil at a concentration ranging from 0.05% to 3% (w/w), preferably ranging from 0.1% to 1% (w/w), more preferably ranging from 1% to 3% (w/w).

The method of the present invention is not limited by the type of surfactant or carrier oil used. One of ordinary skill in the art will be able to select the appropriate surfactant, dispersed phase and carrier oil based on the desired properties of the droplets and reaction conditions used.

Surfactants, also named emulsifying agents, act at the water/oil interface to prevent (or at least to decay) separation of the phases.

In an embodiment, the carrier oil is selected from the group consisting of fluorinated oil such as FC40 oil (3M®), FC43 (3M®), FC77 oil (3M®), FC72 (3M®), FC84 (3M®), FC70 (3M®), HFE-7500 (3M®), HFE-7100 (3M®), perfluorohexane, perfluorooctane, perfluorodecane, Galden-HT135 oil (Solvay Solexis), Galden-HT170 oil (Solvay Solexis), Galden-HT110 oil (Solvay Solexis), Galden-HT90 oil (Solvay Solexis), Galden-HT70 oil (Solvay Solexis), Galden PFPE liquids, Galden® SV Fluids or H-Galden® ZV Fluids; and hydrocarbon oils such as Mineral oils, Light mineral oil, Adepsine oil, Albolene, Cable oil, Baby Oil, Drakeol, Electrical Insulating Oil, Heat-treating oil, Hydraulic oil, Lignite oil, Liquid paraffin, Mineral Seal Oil, Paraffin oil, Petroleum, Technical oil, White oil, Silicone oils or Vegetable oils. In a particular embodiment, the carrier oil is a fluorinated oil. In a more particular embodiment, the carrier oil is HFE-7500 oil.

In a preferred embodiment, the depth of all channels on the microfluidic chip is the same and is in the range from 1 µm to 1000 µm, preferably in the range 50-500 µm and more preferably in the range of 20-300 µm, and even more preferably in the range of 10-100 µm.

In a further embodiment, the method of the invention further comprises collecting fluid droplets off-chip.

In another embodiment, the collected droplets are broken thereby releasing capsules into surrounding media. This can be achieved by destabilizing the droplet water-oil interface using chemical means or using electro-coalescence, temperature, dilution, etc. In this particular embodiment, the droplet water-oil interface is destabilized by mixing the emulsion with chemical such as fluorinated octanol.

In one exemplary embodiment, the capsules are composed of semi-permeable shell and liquid-like core.

In a preferred embodiment, the semi-permeable shell is a hydrogel composed of PEGDA, and liquid-like core is enriched in Dextran.

In one exemplary embodiment, the cells, biochemical and biological compounds are introduced into liquid droplets/capsules by supplying the said entities in:
(i) In the "Phase I solution";
(ii) In the "Phase II solution";
(iii) In both solutions.

In the method of the invention, the species encapsulated in capsules are exposed to different biochemical environment by suspending the said capsule in desired aqueous solution or polar solvent.

In another aspect of the invention, the species encapsulated in capsules are reacting with chemical, biochemical or biological compounds present in aqueous solution.

In another exemplary embodiment, the encapsulated cells are lysed inside the capsules.

In another example, the material of lysed cells is fully or partially retained inside the capsules.

In yet another example, the reagents that were used to lyse the encapsulated cells are replaced by suspending capsules in a different aqueous solution.

In one exemplary embodiment, the nuclei acids of lysed cells are amplified enzymatically. In one specific embodiment the nucleic acids are amplified using phi29 DNA polymerase, yet in another exemplary embodiment the nuclei acids of lysed cells are amplified enzymatically by PCR. Obviously, other enzymes (e.g. Klenow, Bst, Bsm polymerases) are also possible to use for nucleic acid analysis, replication and amplification.

In one exemplary embodiment, the mRNA of lysed cells is converted to cDNA by reverse transcription reaction. In one specific embodiment the cells encapsulated in capsules are lysed and their mRNA is converted to cDNA using reverse transcriptase.

In the method of the invention DNA and/or RNA of lysed cells can be modified/treated using chemical or biochemical means. For example, add poly(A) tail to nucleic acids, add nuclei acid barcodes, add indexes, ligate adapters, digest, fragment, etc.

In the method of the invention the cDNA of encapsulated individual cells can be tagged (barcoded) with barcoded poly(T) primers.

In the method barcoded poly(T) primers can carry cell barcode, molecular barcode (unique molecular identifier), sequencing adapter, poly-dT part and/or other parts as required for barcoding reaction.

In another exemplary embodiment the cDNA of lysed cells is amplified enzymatically by PCR inside or outside the capsules.

In the method of the invention the lysis and nucleic acid amplification is performed on the same encapsulated cells by performing sequential multi-step reactions.

In one preferred embodiment the capsules are used for genotypic analysis of individual cells.

In yet another preferred embodiment, the encapsulated cells are maintained alive over extended periods of time to perform phenotypic analysis of individual cells.

In another exemplary embodiment, the encapsulated cells are cultivated over extended periods of time. In one specific exemplary embodiment, the encapsulated cells are screened for biological activity (e.g. metabolic activity).

In one exemplary embodiment, the biochemical and biological molecules entrapped inside the particles are released by dispersing particles into a surrounding fluid such as biological buffer, water and/or other aqueous solutions.

In exemplary embodiment, the phenotypic and/or genotypic analysis is performed on encapsulated cells and/or their material.

In exemplary embodiment, the above methods are carried out but not limited to using a microfluidics system. The microfluidic system may be installed by the skilled person.

The following examples of the invention is given for purposes of illustration and not by way of limitation.

EXAMPLES

Experimental Methods

Materials and Reagents

Device fabrication and operation. The polydimethylsiloxane (PDMS) microfluidic device was fabricated and operated using standardized protocol as described (Mazutis et al., Nature Protocols, 2017).

Preparation of ATPS. All chemicals were ordered from Sigma-Aldrich and Fisher Scientific. ATPS droplets were prepared using 5.5% (w/v) Dextran (MW 500K), 3% (w/v) PEGDA (MW 8K), 3% (v/v) PEGDA (MW 575), 0.1% (w/v) LAP (lithium phenyl-2,4,6-trimethylbenzoylphosphinate), 1× DPBS. Modified concentrations of PEGDA (MW 8K) and PEGDA (MW 575) as well as modified polymers could be used. The solutions containing all ingredients were mixed and centrifuged in a table centrifuge at maximum speed for 30 minutes to induce liquid-liquid phase separation Preparation of hydrogel beads. The mixture of 6% (v/v) PEGDA (MW 575) and 0.1% (w/v) LAP in 1× DPBS was used for hydrogel bead preparation and bacteria embedding following hydrogel bead production protocol as previously described (Mazutis et al., Nature Protocols, 2017).

Preparation of microbial cells. *Escherichia coli* (MG1655 and DH5a), *Bacillus subtilis* (SHgw) as well as pBHR68 and pTZ18R plasmids were kindly provided by Prof. R. Meškys (Vilnius University, Institute of Biochemistry, Lithuania). DH5α strain was transformed with pBHR68 plasmid, harboring three genes (phaC, phaA and phaB) from PHB synthesis pathway. As a negative control, DH5α strained transformed with pTZ18R vector was used. Prior the encapsulation bacteria were suspended in Dextran-rich phase and when needed supplemented with 100 µg/mL Ampicillin.

Emulsification. As exemplified in FIG. 1 droplets, hydrogel beads and capsules were generated using microfluidics chip 20 µm height and having a nozzle 15 µm wide. Typical flow-rates used were: PEGD(M)A-rich phase—50 µL/hr, Dextran-rich phase or 1× DPBS (with/without bacteria)—50 µL/hr and droplet stabilization oil (Droplet Genomics, DG-DSO-20)—350 µL/hr. For larger size capsule generation 50 µm height microfluidics chip was used with the following flow rates: PEGD(M)A-rich phase—140 µL/h, Dextran-rich phase with cells—70 µL/h and droplet stabilization oil (Droplet Genomics, DG-DSO-20)—600 µL/h. Due to increased viscosity of biphasic system, droplet breakup by jetting mechanism could be observed, which could shift to dripping mode by adjusting the flow rates of a system.

Cross-linking. Emulsions were collected in a 1.5 ml tube and immediately cross-linked by exposure under 365 nm wavelength using High-Intensity UV Inspection Lamp, UVP (UVP, 95-0127-01) for 2.5 minutes. ATPS droplets for bacteria culture experiments were exposed to 405 nm laser (1 W/cm$^2$) for 20 seconds. After hardening the PEGDA shell resulting capsules were recovered from the emulsion using commercial emulsion breaker (Droplet Genomics, DG-EB-1).

Lysis and DNA amplification in hydrogel beads and capsules. Lysis of encapsulated bacteria was performed by suspending hydrogel beads or capsules in lysis buffer containing: 50 U/µL Ready-Lyse™ Lysozyme Solution (Lucigen, R1804M), 200 µg/mL Proteinase K (Invitrogen, AM2546), 0.1% (v/v) Triton X-100 (Sigma-Aldrich, T8787-100 ML), 10 mM Tris-HCl [pH 7.5] and 1 mM EDTA. Hydrogel beads and capsules suspended in lysis buffer were incubated for 30 min at 37° C. followed by additional 30 min incubation at 50° C. After lysis, hydrogel beads and capsules were washed three times in a Washing buffer (10 mM Tris-HCl [pH 7.5] and 0.05% (v/v) Triton X-100). MDA reaction was then performed by suspending capsules and hydrogel beads in MDA reaction buffer containing 0.5 U/µL phi29 DNA polymerase (Thermo Scientific, EP0092) and 0.002 U/µL, inorganic pyrophosphatase (Thermo Scientific, EF0221) following manufacturer's recommendations. Bulk-like PCR was used to amplify specific regions of 16S rRNA, kdsC and ompA genes corresponding to 320, 567 and 1050 bp fragments, respectively. Each amplification was performed for 35 cycles with KAPA PCR kit (KAPABiosystems, KK2602) according to manufacturer's recommendations. In all enzymatic reactions, the close-packaged capsules and hydrogel beads occupied approx. 40-50% of the final reaction volume.

Lysis and DNA amplification in droplets. To perform E. coli and B. subtilis lysis in droplets, bacteria were resuspended in 10 mM Tris-HCl [pH7.5] and co-encapsulated with Ready-Lyse™ Lysozyme Solution, Triton X-100, phi29 DNA polymerase buffer and DTT at the final concentration of 50 U/µl, 0.1% (v/v), 1× and 1 mM, respectively. When cell lysis and MDA reaction was performed simultaneously, the final reaction composition was: 1× Reaction Buffer for phi29 DNA polymerase, 25 µM Exo-resistant random primer (Thermo Scientific™, SO181), 1 mM dNTP Mix (Thermo Scientific™, R0192), 1 mM DTT (Thermo Scientific™, 707265 ML), 0.1% (v/v) Triton X-100 (Sigma-Aldrich, T8787-100 ML), 50 U/µl Ready-Lyse™ Lysozyme Solution (Lucigen, R1804M), 0.5 U/µl phi29 DNA polymerase (Thermo Scientific, EP0092) and 0.002 U/µl inorganic pyrophosphatase (Thermo Scientific, EF0221). The encapsulation conditions as well as MDA reaction conditions were the same as with capsules.

Imaging of processed bacteria. Droplets, hydrogel beads and capsules were stained with 1× SYBR Green I dye (Invitrogen, S7563) and analyzed under inverted fluorescence microscope using the following settings: magnification—10×, filter—FITC, gain—1, 20% intensity of blue light source used for excitation and exposure time were varied depending on the analysis step. Images were recorded using digital camera (Nikon eclipse Ti at 12-bit resolution).

Capsule analysis by flow cytometry. The capsules were stained with 1× SYBR Green I dye and analysed on Sapphire microfluidics platform (Droplet Genomics, DG-SPH-1). A total of 150.000 capsules were measured using a 488 nm diode laser (1 mW) focused to a 40 µm diameter channel.

Capsule solubilization and DNA extraction. Capsules were dissolved in the presence of 1 M NaOH at 50° C. for 10 minutes and then neutralized by adding equimolar amount of 1M Acetic Acid. PCR products from dissolved capsules were extracted and concentrated using 1.8× Agencourt AMPure XP magnetic beads (Beckman Coulter, A63881) and analyzed on 1% agarose gel.

Bacteria cultivation inside capsules. All bacteria growth experiments were performed in disposable 30×15 mm Petri dishes. MG1655 bacteria encapsulated in capsules, hydrogel beads or droplets were cultivated in LB medium at 37° C. for 4-8 h, while the media for transformed DH5α strain was supplemeted with 100 µg/mL Ampicillin. After reaching exponential growth (4-6 h), polyhydroxybutyrate (PHB) synthesis in DH5α was induced by adding 1 mM isopropyl β-D-1-thiogalactopyranoside (Thermo Scientific, R1171) followed by incubation at 30° C. for 8 h.

Imaging of encapsulated bacteria. Capsules and droplets with MG1655 cells were stained with 1× SYBR Green I dye and analyzed under inverted fluorescence microscope. DH5α strain was stained for 10 minutes with Nile Red (0.5 µg/mL) and analyzed using the following settings: magnification—10×, filter—TXRED, gain—1, exposure time—100 ms, 40% intensity of green light source for excitation. The second round of imaging was performed after lysis (without the additional staining with Nile Red) using the same conditions to evaluate the changes of fluorescence. For dual DH5α imaging, capsules were stained repeatedly with Nile Red and SYBR Green I dyes. Images were taken using following settings: magnification—1×, filters—FITC and TXRED, gain—1, exposure time—10 ms for FITC filter and 40 ms for TXRED, 20% and 40% intensity of blue and green light source for excitation, respectively. Images were recorded using Nikon eclipse Ti camera at 12-bit resolution on an inverted fluorescence microscope.

Data processing. Fluorescence data was obtained by manually outlining droplets from brightfield images and then using these masks to segment fluorescence images. Data was managed and analyzed using R (v.3.5.3) and R studio (v.1.1.463). Capsule fluorescence was normalized to image background and image acquisition settings were kept the same during comparative experiments. Fluorescence was reported as logarithmic values to control the dynamic range, normalize dispersion and allow comparing dim and bright objects. Positive/Negative capsule identification was achieved based on fluorescence data histogram analysis. T-testing was used for statistical significance measurements, where stars indicate p-value ranges: *(0.05-0.01), (0.01-0.001), *(P<0.001).

RESULTS

Figure 2:
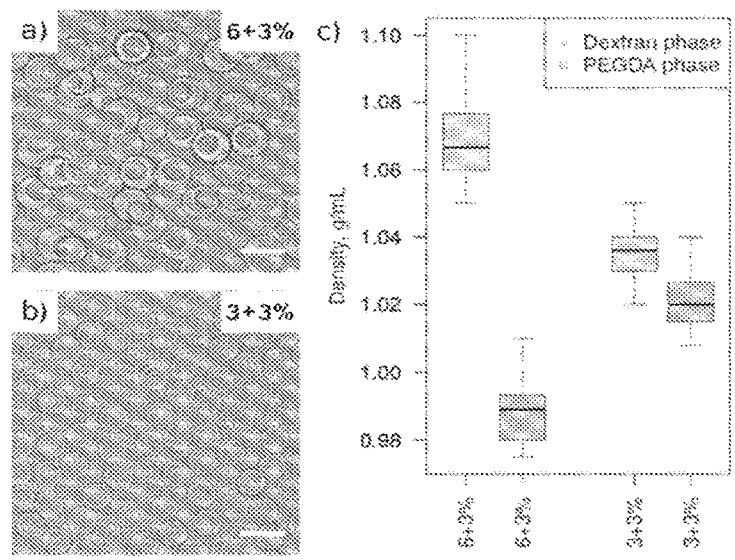
FIG. 2. Concave versus core-shell capsule formation. In panel (a) capsules were prepared using the composition of 6% PEGDA (MW 8K) and 3% PEGDA (MW 575), while in panel (b) 3% PEGDA (MW 8K) and 3% PEGDA (MW 575) were used. (c) Boxplots demonstrate the difference in density between PEGDA and Dextran phases. Scale bars, 50 μm, boxplots are derived from samples of N>25 measurements.
Figure 3:
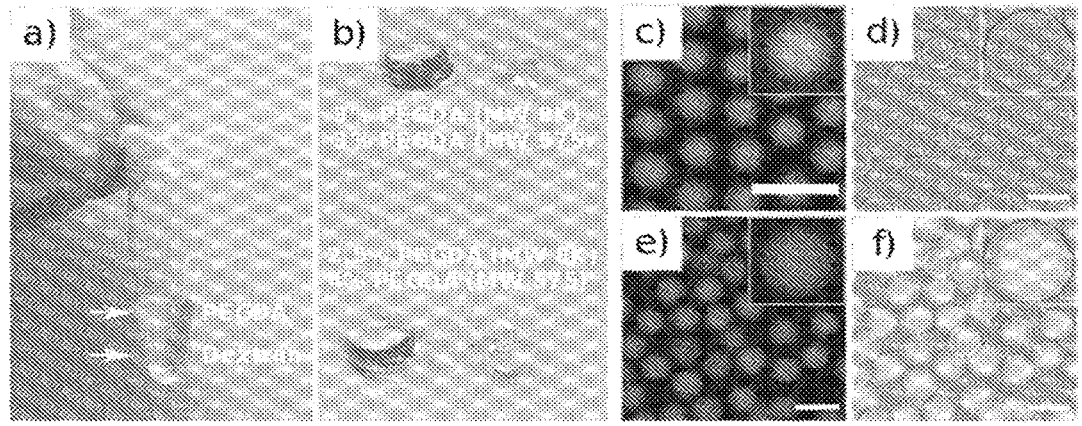
FIG. 3. Capsule production. Panel (a) shows PEGDA and Dextran phase separation after centrifugation, where Dextran phase was stained with 0.1% (w/v) fluorescein isothiocyanate-Dextran (MW 500K). (b) Separation of two phases after photo-polymerization, where PEGDA-rich phase formed hardened hydrogel shell and Dextran-rich phase became more viscous. (c) ATPS droplets showing dextran phase partitioning into the core. Panels (d) and (e) show capsules under bright field and fluorescent microscope, respectively, whereas (f) is merged images. Scale bars, 50 μm.

In the current state-of-the-art one of the biggest challenges for implementing capsule formation based on aqueous two-phase system (ATPS) is an inconsistent and non-uniform shell formation (Ma, S. et al. Small 8, 2356-2360 (2012). Mytnyk et al., RSC Adv., 2017, 7, 11331-11337). We have noticed that the capsule core tends to migrate towards the outer interphase before shell gelation could occur, leading to a concave particle topology. As a result, a significant fraction of capsules released their encapsulated material prematurely, contained uneven or ruptured shells (FIG. 2). Obviously, such defective capsules would hinder many biological applications that mandate efficient sample encapsulation, retention and processing reproducibility. Since the capsule's shell uniformity depends on concentricity of ATPS droplets, we postulated that the density mismatch between the core and shell phases was driving the core of-centre. We show that by reducing the density difference between the two aqueous phases enables consistent generation of monodisperse and concentric ATPS droplets (FIGS. 1 and 2). To solidify the shell of ATPS droplets en masse we used photo-illumination, as a chemically neutral measure to induce fast (~2 min) PEGDA polymerization and form a hardened shell. The resulting capsules contained aqueous (liquid-like) core enriched in Dextran phase and solidified hydrogel-shell, enriched in PEGDA. We noticed that the core of capsules becomes more viscous after photopolymerization (FIG. 3) presumably due to the presence of residual PEGDA and/or formation of a weak hydrogel mesh, however that did not have a negative effect on biological assays presented herein.

To achieve the right balance between capsule uniformity, concentricity and mechanical stability we arrived at the composition containing blends of longer (MW 8K) and shorter (MW 575) polyethylene glycol diacrylate (PEGDA) polymers, and aqueous Dextran (MW 500K) solution (see Experimental Methods). Whereas, the longer PEGDA was required for efficient phase separation, the shorter PEGDA was added to increase shell stiffness and improve capsule mechanical stability. The capsules withstood mechanical stress and remained highly uniform with less than 2% size variation after washing in aqueous buffer multiple times (FIG. 1*e*). Furthermore, capsules sustained multiple temperature cycles during PCR as well as shear forces generated during flow cytometry (see below). In the following we showcase a few examples of semi-permeable capsule use in multi-step procedures for genotypic and phenotypic analysis of individual bacteria cells in a massively parallel fashion.

Example 1—Nucleic Acid Analysis Using Capsules

Nucleic acid analysis of individual bacterial cells in water-in-oil emulsions can be hindered by the preceding cell lysis step. Chemical conditions required to break the cell wall of microorganisms can interfere with downstream reactions, leading to inefficient or non-uniform DNA amplification, or in case of droplet microfluidics—emulsion instability. Bacterial lysis steps can be particularly problematic for isothermal nucleic acid amplification methods (e.g. MDA) or working with gram-positive bacteria, which are known to be much more resistant to thermolysis. To circumvent above mentioned limitations, the state-of-the-art techniques use hydrogel beads, where the key feature relies on bacteria embedding into a hydrogel-mesh so that harsh but efficient lysis can be performed separately from the subsequent enzymatic steps (Spencer, S. J. IMSE. J., 427-436 (2016); Tamminen, M. V. & Virta, M. P. J. *Front. Microbiol.* 6, 1-10 (2015); Novak, R. et al. *Angew. Chemie—Int. Ed.* 50, 390-395 (2011); Scanlon T. C., et al *Biotechnol. Bioeng.* 111: 232-243 (2014). These hydrogel-bead based systems have convincingly demonstrated that semi-permeable carriers can be used for multi-step biochemical reactions. However, these methods often suffer from complicated processing conditions, including multiple compartment modifications (Tamminen, M. V. & Virta, M. P. J. *Front. Microbiol.* 6, 1-10 (2015), additional emulsification steps (Spencer, S. J. IMSE. J., 427-436 (2016); Novak, R. et al. *Angew. Chemie—Int. Ed.* 50, 390-395 (2011)) or complex microfluidic operations (Lan F., *Nat Biotechnol.* July; 35(7): 640-646, (2017)) and more importantly a significant bacteria loss during hydrogel bead production.

Figure 4:
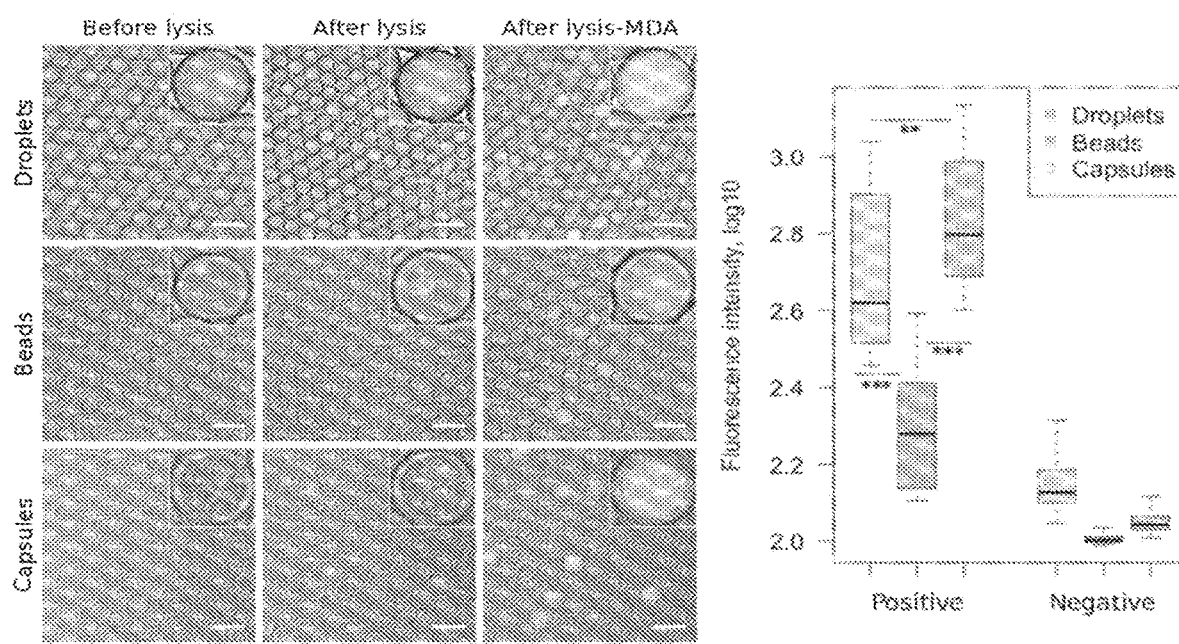
FIG. 4. Comparison of multi-step processing of encapsulated E. coli cells in three microfluidic formats: 1) droplets (water-in-oil emulsion), 2) hydrogel beads and 3) capsules. On the left, merged images showing fluorescence intensity of each assay before and after cell lysis and after MDA reaction. Following exposure times were used for fluorescent microscopy: before and after lysis—1 s, after MDA—10 ms. Bacteria cells, suspended in 10 mM Tris-HCl [pH 7.5] were co-encapsulated with Lysozyme, Triton X-100, Phi29 DNA Polymerase buffer and DTT (see Experimental Methods). E. coli containing hydrogel beads were produced with 6% (v/v) PEGDA (MW 575), whereas for capsules production the blend contained 3% (w/v) PEGDA (MW 8K), 3% (v/v) PEGDA (MW 575) and 5.5% (w/v) Dextran (MW 500K) was taken. To visualize DNA, the samples were stained with 1× SYBR Green I dye and analyzed under fluorescent microscope using the following exposure times: before and after lysis—1 s, and after MDA—10 ms. On the right, boxplots representing mean fluorescence intensity in positive and empty post-MDA compartments. Boxplots were derived from N>500 measurements, stars show statistical significance based on t-test. Scale bars, 50 μm.
Figure 5:
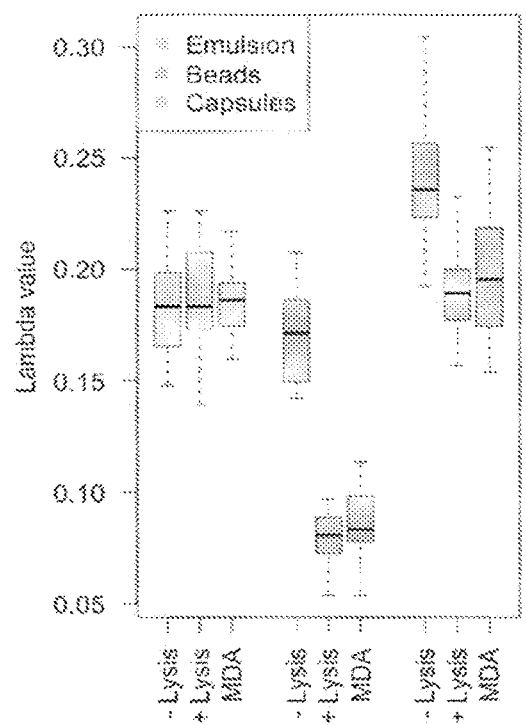
FIG. 5. Lambda value (occupancy) measurements of E. coli encapsulation, lysis and MDA reaction in three microfluidic formats: 1) water-in-oil emulsion (green), 2) hydrogel beads (blue), and 3) capsules (red). Boxplots are derived from samples of N>500 measurements. Note, hydrogel beads showed a significant drop in lambda value after lysis step.
Figure 6:
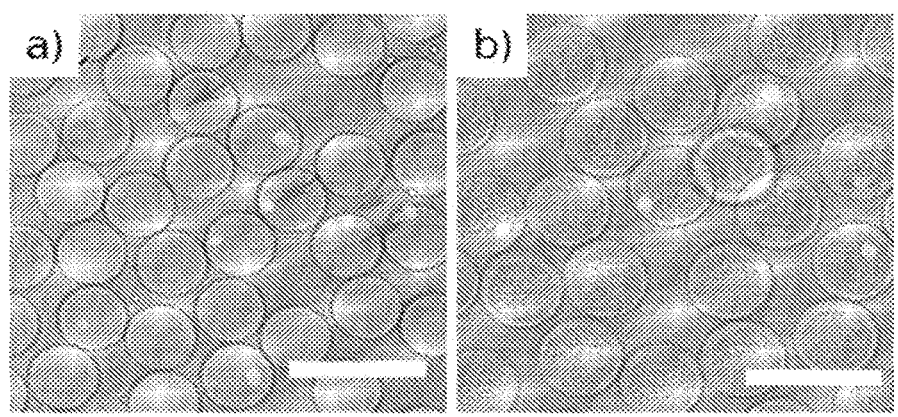
FIG. 6. E. coli distribution inside hydrogel beads and capsules. (a) Partition of encapsulated E. coli cells in hydrogel beads, where blue arrows indicate bacteria close to the interphase. (b) Partition of encapsulated E. coli cells in capsules, where red arrows indicate bacteria close to the Dextran-PEGDA interface. Scale bars, 50 μm.

To demonstrate the unique advantages provided by semi-permeable capsules for microbiology we compared the efficiency of MDA reaction on individual *E. coli* bacterial cells in three different formats; 1) water-in-oil droplets, 2) hydrogel beads and 3) semi-permeable capsules (FIG. 4). For each test, a suspension of *E. coli* cells was encapsulated in 10 picoliter (pL) volume droplets together with reagents required for hydrogel bead, or capsule generation (refer to Experimental Methods for further details). After encapsulation, the observed occupancy by *E. coli* cells in each assay followed Poisson distribution and was ~0.2 (FIG. 5) suggesting that there is no significant encapsulation bias between different droplet assays. However, significant differences emerged after the cell lysis step. Whereas the number of positive compartments in water-in-oil droplets and capsules remained similar, hydrogel-bead based assay experienced ~50% cell loss (FIG. 5). Such drastic drop in occupancy can be explained by bacteria's tendency to localize at the proximity of the water-oil interphase (FIG. 6). As a result, the genetic material released during lysis step becomes susceptible to diffusion out of the hydrogel mesh and eventual loss. Noteworthy, in ATPS droplets the cell partitioning can be controlled by adjusting the ionic species or electrostatic potential of Dextran-PEGDA phases amongst other components (Cabral, J. M. S., *Adv. Biochem. Eng. Biotechnol.* 106, 151-171 (2007); Zijlstra, G. M., Systems Biotechnol. Prog., 1996, Vol. 12, No. 3).

Integrated fluorescence measurements showed that the MDA reaction on individual *E. coli* cells was 3-times more efficient in capsules as compared to hydrogel beads (FIG. 4, blue and red boxplots). The higher reaction yield in capsules can be attributed to the liquid-like core, which does not confine the long DNA molecules (>10 kb) synthesized by phi29 DNA polymerase. In hydrogel beads, however, the newly synthesized DNA is embedded in the hydrogel mesh and is physically confined, thus leading to less efficient replication. Similarly, the MDA reaction yield in water-in-oil droplets was 2-times higher than in hydrogel-beads (FIG. 4, green and blue boxplots), supporting the notion that DNA synthesis reaction is more efficient in a liquid rather than a hydrogel state. Comparing the MDA reaction yield in capsules vs. water-in-oil droplets (FIG. 4, green and red boxplots) we observed mild reaction improvement in capsules, which can be explained by exchange of MDA reaction components through a semi-permeable membrane. In other words, the amount of MDA reagents (dNTPs, primers, enzyme) in capsule-based assay is not confined by the droplet volume, but can be continuously replenished through a semi-permeable membrane. Capsule advantage over droplets could be also explained by more efficient bacteria lysis: the capsules were suspended in lysis buffer containing Lysozyme and Proteinase K enzymes, while in microdroplet assay the use of Proteinase K is prohibitive due to incompatibility with MDA reaction.

Figure 7:
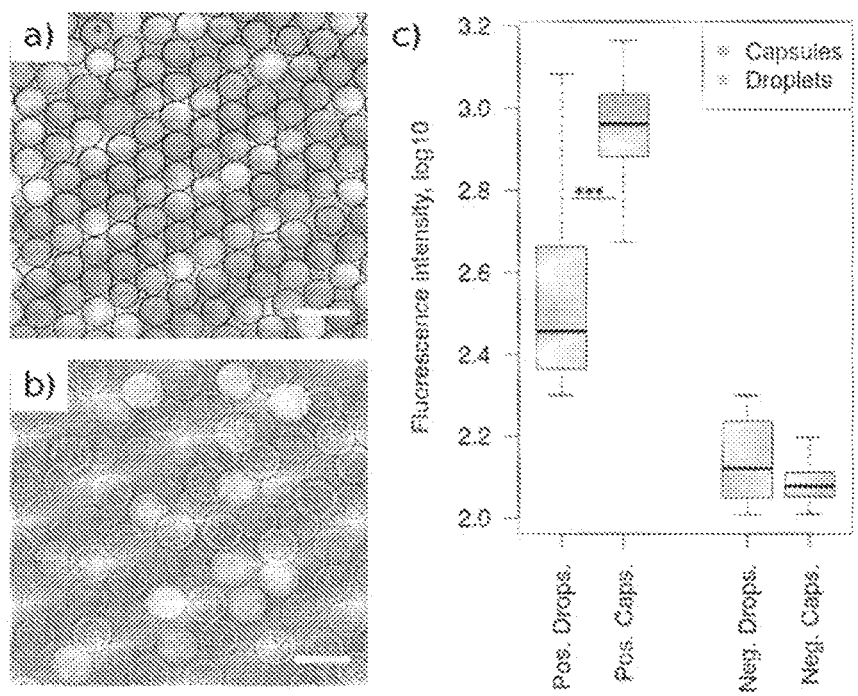
FIG. 7. Comparison of MDA reaction yield on single B. subtilis in water-in-oil emulsion and in capsules. Merged fluorescence and bright field images of (a) post-MDA droplets and (b) post-MDA capsules. (c) Comparison of MDA reaction efficiency based on fluorescence intensity in capsules (red) and in droplets (green). Boxplots are derived from samples of N>500 measurements, stars show statistical significance based on t-test. Scale bars, 50 μm.
Figure 8:
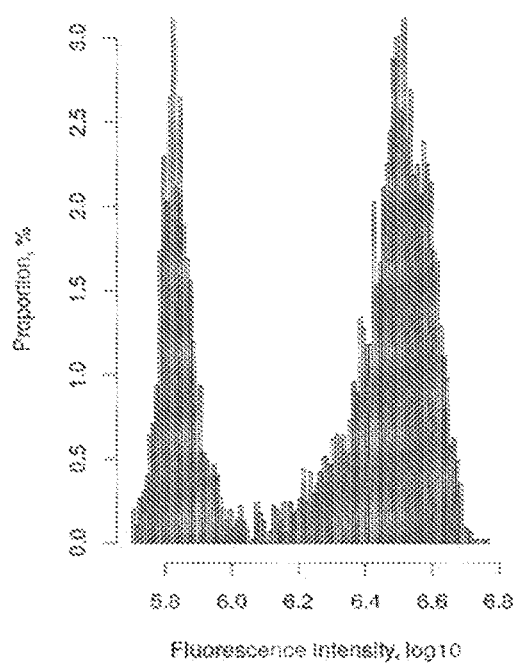
FIG. 8. Post-MDA capsule analysis by flow cytometry. Histogram shows 150.000 capsule fluorescence distribution, where the intensity <6.1 represents negative and >6.1 positive capsules.

We anticipated that the differences in single genome amplification efficiency will be also pronounced on gram-positive microorganisms whose lysis require harsher conditions that are either inhibitory or detrimental to subsequent enzymatic steps. To verify this, we encapsulated and subsequently lysed *B. subtilis* bacteria with a mixture of Lysozyme and Proteinase K enzymes (the same conditions as used for *E. coli*). We removed lysis reagents by washing the capsules and then dispersed capsules in the MDA reaction mix to initiate DNA synthesis. The post-MDA capsules were analyzed microscopically (FIG. 7) and by flow cytometry (FIG. 8). As expected, the harsher cell lysis conditions that was possible to use with capsules led to approx. 3-times higher MDA reaction yield, when compared to standard conditions using water-in-oil droplets. Furthermore, there was a better separation between positive and negative compartments (higher signal-to-noise ratio) as well as higher uniformity of MDA reaction yield (FIG. 7). Combining the MDA results obtained on *B. subtilis* and *E. coli* bacteria we conclude that capsules not only efficiently retain the genetic material released upon lysis but more importantly can be processed in a series of enzymatically incompatible reactions in order to generate increased yields of amplified gDNA.

Figure 9:
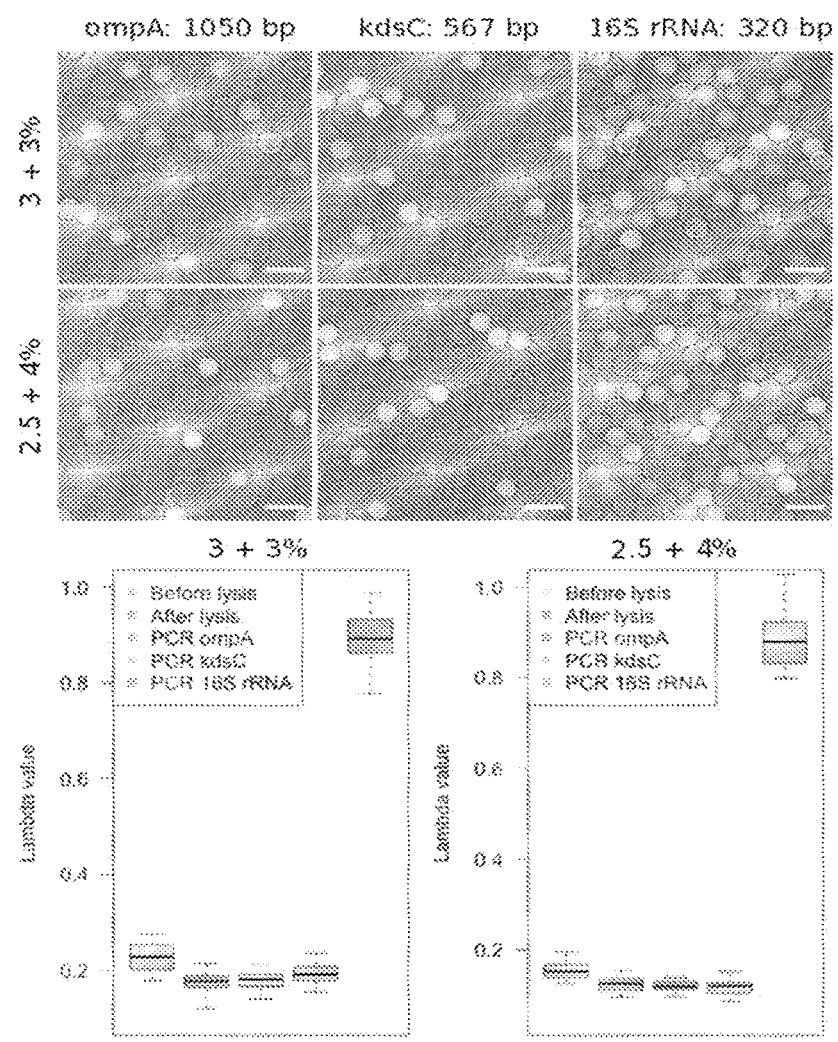
FIG. 9. Analysis of PCR amplicon retention inside capsules. Above, merged images showing the capsules after the synthesis of different length PCR amplicons: ompA (1050 bp), kdsC (567 bp), 16S rRNA (320 bp). Below, boxplots, representing lambda value (the mean number of bacteria in each capsule following Poisson distribution) before and after cell lysis, and after PCR with corresponding PCR amplicons. Histograms are derived from samples of N>500 measurements. Scale bars, 50 μm.
Figure 10:
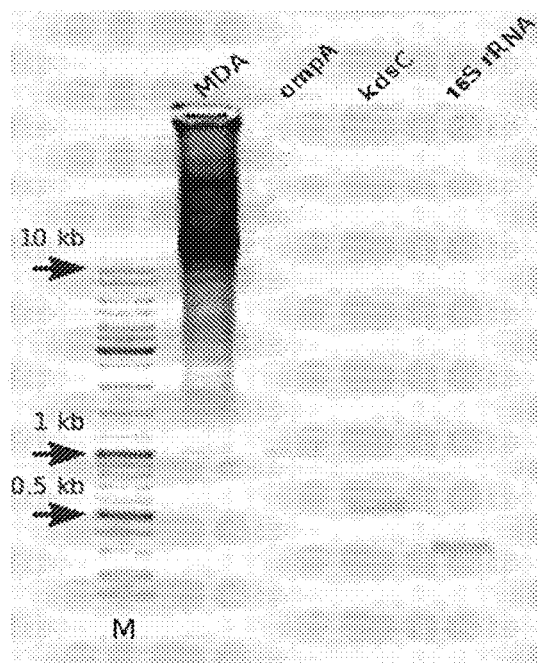
FIG. 10. DNA recovery from post-PCR and post-MDA capsules by alkaline treatment. 5 μl of capsules, harboring MDA product or one of three amplicons (320, 567 or 1050 bp.) were dissolved in 1M NaOH, neutralized with 1M acetic acid, and released DNA was purified/concentrated using AMPureXP magnetic beads. The expected size of ompA, kdsC and 16S RNA amplicons is 1050, 567 and 320 bp, respectively. M—GeneRuler DNA Ladder Mix (SM0331).

The results presented here convincingly prove that capsules provide efficient physical barrier for retaining the large molecular weight biomolecules such as bacterial chromosome, or amplified gDNA. To answer the question, what is the smallest DNA fragment that capsules can still retain: we generated 320, 567 and 1050 bp. long DNA fragments by PCR and followed their diffusion between the compartments. As illustrated in FIG. 9 the capsules efficiently retained 567 bp. DNA fragments, the size of which approximately corresponds to MW 340K. Smaller DNA fragments (320 bp. corresponding to approx. MW 190K) diffused between the capsules as witnessed by appearance of low fluorescence compartments and increase in post-PCR occupancy value. Based on these results and previous reports (Aimar, P., Meireles, M. & Sanchez, V. A. *J. Memb. Sci.* 54, 321-338 (1990)) we estimated the average pore size of the shell to be in the range of 20-50 nm. Finally, to confirm that the expected size DNA fragments were indeed generated during PCR we dissolved the capsules in alkaline solution, extracted DNA and performed electrophoresis. As expected, PCR was highly specific and produced expected size DNA fragments (FIG. 10).

Example 2—Cell Cultivation and Phenotypic Analysis Using Capsules

In addition to nucleic acid amplification and analysis (Example 1) many microbiology assays also rely on phenotypic characterization. This commonly requires bacterial culture, induced gene expression and subsequent analysis of proteins or metabolites that serve as a phenotypic readout. Below we demonstrate the use of semi-permeable capsules for cell culture and screening for metabolic activity in colonies originating from a single bacterium.

Figure 11:
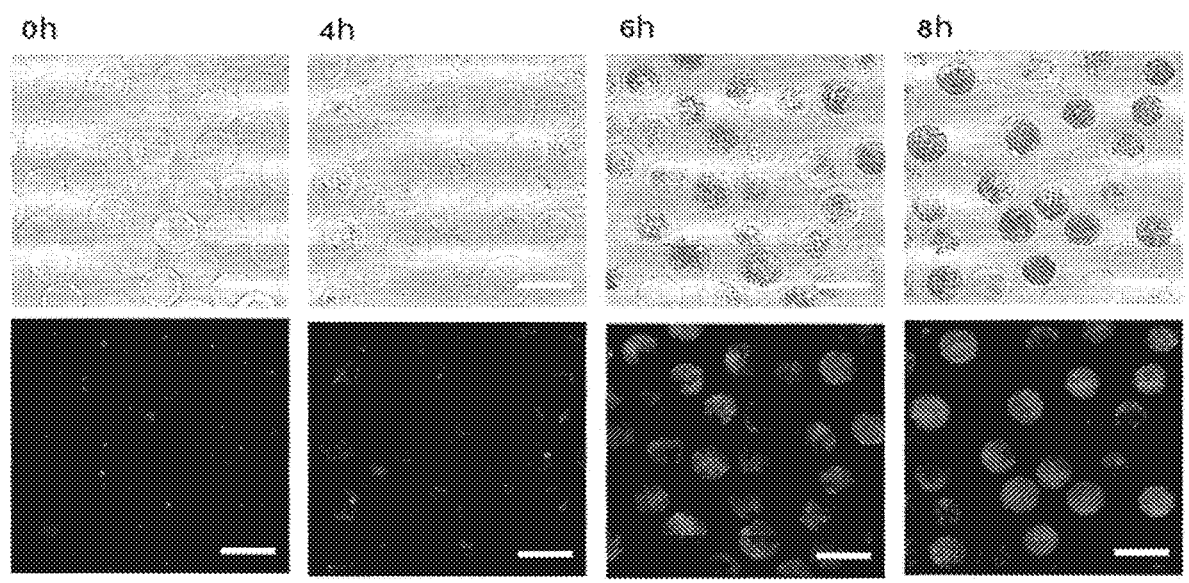
FIG. 11. E. coli (MG1655) cultivation in capsules with the composition of 3% (w/v) PEGDA (MW 8K), 3% (v/v) PEGDA (MW 575) and 5.5% (w/v) Dextran (MW 500K). The cell growth was monitored for 8 hours. Samples were analyzed by brightfield and fluorescence microscopy after staining with 1× SYBR Green I. Exposures times: 0 h-400 ms, 4 h-8 h-10 ms. Scale bars, 50 μm.
Figure 12:
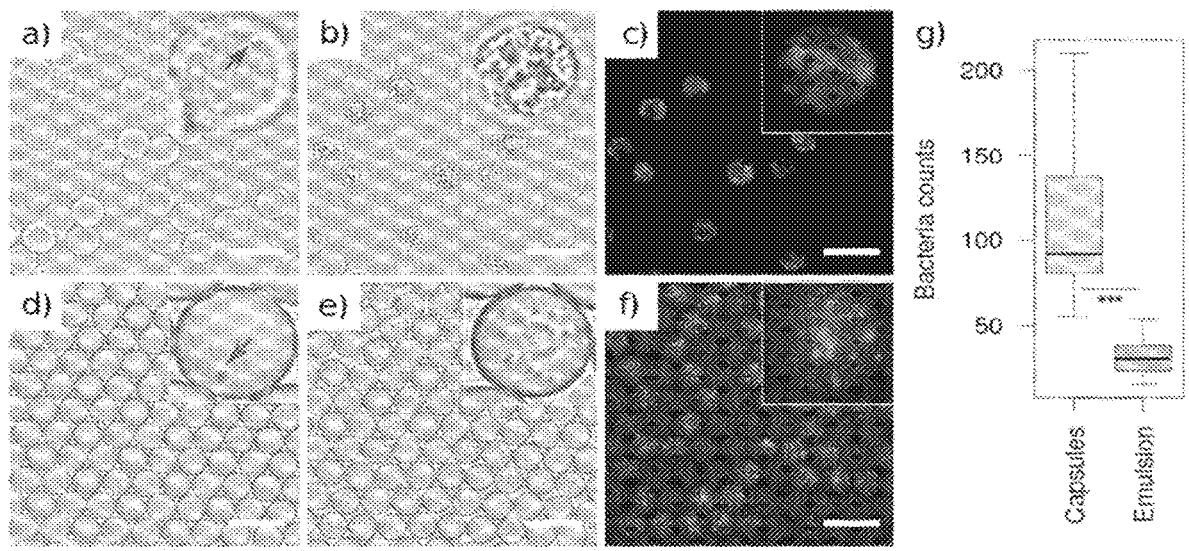
FIG. 12. Comparison of E. coli (MG1655) bacteria growth in capsules and in droplets. Panels (a) and (d) show capsules and droplets at 0 h, (b) and (e)—after 4 h of cell culture at 37° C. Panels (c) and (f) represent fluorescent bacteria from images (b) and (e) after staining with SYBR Green I dye. (g) Boxplots, representing bacteria counts after 4 hours of incubation. Exposure time for (c) image was 10 ms, and for (f)—100 ms. Boxplots are derived from samples of N>20 measurements, stars show statistical significance based on t-test. Scale bars, 50 µm.

We first evaluated whether capsules can be used as micro-chemostats for cell culture applications. For that purpose we encapsulated *E. coli* bacteria using the same microfluidics device as indicated in FIG. 1 and then immersed the capsules in growth medium for 4 hours at 37° C. We used time-lapsed microscopy to continuously monitor individual clones, their growth and expansion into isogenic micro-colonies (FIG. 11). Combining this digital data with fluorescence analysis we estimated that in 4-hours at 37° C. individual clones expanded into micro-colonies comprising on average 90-cells (FIG. 12). In comparison, cell culture in water-in-oil droplets generated smaller microcolonies comprising on average 30-cells. Furthermore, analyzing bacteria in capsules based on fluorescence signal was considerably easier, as the background from auto fluorescent LB media could be removed in a few washing steps, leading to an increased signal-to-noise ratio (FIG. 13).

Having shown the cell growth and isogenic colony formation we then applied capsules for phenotypic analysis of bacteria producing polyhydroxybutyrate (PHB)—an environmentally important biodegradable plastic. Identifying the metabolic products of microorganisms can be a challenge as it may require simultaneous phenotypic (PHB synthesis) and genotypic (nucleic acid quantification) readouts. To demonstrate that such analysis is possible using semi-permeable capsules we used *E. coli* (DH5α) strain transformed with pBHR68 vector, harboring genes (phaC, phaA and phaB) for PHB synthesis. We loaded cells in microfluidic capsules, cultivated them into micro-colonies and then induced PHB synthesis by adding IPTG. We verified PHB formation in live cell culture using Nile Red dye, which stains PHB granules (FIG. 14*a* and *c*). Being a lipophilic dye, Nile Red also binds to cell membranes giving a high fluorescent signal in both positive and negative control samples (FIG. 14*b* and *c*). To circumvent the background fluorescence resulting from non-specific staining we dissolved cell membranes with lysis reagents and washed capsules several times greatly increasing the analytical differentiation of positive and negative clones (FIG. 14*e-g*). Furthermore, using dual staining, Nile Red dye for PHB granules and SYBR Green I for gDNA, enabled normalization of PHB levels to bacteria count (FIG. 15), which is crucial for screening efficient producers rather than fastest growing clones.

Example 3—Reverse Transcription and Polymerase Chain Reaction in Capsules

Mammalian Cell Encapsulation in Capsules

K-562 cells were re-suspend in 100 μL of Dextran-rich phase containing 0.4 U/μl RiboLock RNase inhibitor. Final concentration of K-562 cells was ~5*10^5/ml. Then ~100 μm diameter capsules were prepared using the composition as listed below:

| Volume | Material | Final |
|---|---|---|
| 10 μl | 40% (w/w) PEGDMA (MW 8K) | 2% (w/v) |
| 4 μl | 100% PEGDMA (MW 550) | 2% (v/v) |
| 8 μl | 100% PEGDA (MW 575) | 4% (v/v) |
| 44 μl | 25% (w/v) Dextran (MW 500K) | 5.5% (w/v) |
| 4 μl | 5% (w/w) LAP | 0.1% (w/v) |
| 130 μl | 1x DBPS | — |
| 200 μl | Final | |

Reagents were combined, vortexed and centrifuged at maximum speed for 30 minutes. After the separation of two phases (PEGD(M)A and Dextran), the cells were re-suspended in Dextran-rich phase. Encapsulation was performed using 50 μm deep microfluidics device. After encapsulation shell polymerization was induced under 365 nm light for 2.5 minutes. Before releasing capsules, 200-300 μl of 1× DPBS+0.3% (v/v) NP-40 was added on top of emulsion and then capsules released by breaking emulsion with 200-400 μl of 20% (v/v) PFO. Capsules were washed several times followed by the lysis step.

Encapsulated Cell Lysis in Capsules

The cell lysis was performed using the composition listed below:

| Volume | Material | Final |
|---|---|---|
| 30 μl | 10% (v/v) NP-40 | 0.3% (v/v) |
| 10 μl | 20 mg/ml Proteinase K | 200 μg/ml |
| 200 μl | Capsules | |
| 760 μl | 1X DPBS | |
| 1000 μl | Final | |

Capsules were incubated in lysis mix at 37° C. for 30 minutes, washed 3-4 times with 1× DPBS containing 0.3% (v/v) NP-40 to remove Proteinase K. Capsules were stained with SYBR Green I and analyzed under fluorescence microscope before proceeding to the next step.

Encapsulated Cell Treatment With DNase I

DNA removal was performed using the reaction composition listed below:

| Volume | Material | Final |
|---|---|---|
| 50 μl | 10X DNase I Buffer with MgCl2 | 1X |
| 12.5 μl | DNase I, 1 U/μl | 0.025 U/μl |
| 5 μl | RiboLock RI, 40 U/μl | 0.4 U/μl |
| 200 μl | Capsules | — |
| 232.5 μl | Water, nuclease free | — |
| 500 μl | Final | |

Capsules were incubated at 37° C. for 20 minutes, washed 3-4 times in 1× DPBS containing 0.3% (v/v) NP-40 and fraction of capsules was stained with SYBR Green I. Next capsules were processed in reverse transcription and PCR reactions.

RT-PCR on Encapsulated Cells

To perform RT-PCR the capsules were suspended in the buffer those composition is listed below:

| Volume | Material | Final |
|---|---|---|
| 25 μl | 2X Platinum SuperFi RT-PCR Master Mix | 1X |
| 2.5 μl | *ACTB Primer Mix, 10 μM each | 0.5 μM |
| 0.5 μl | Superscript IV RT Mix | — |
| 20 μl | Capsules | — |
| 2 μl | Water, nuclease-free | — |
| 50 μl | Final | |

As a negative control, samples with no RT enzyme but with 2× Platinum SuperFi RT-PCR Master Mix was used. The expected size of ACTB amplicons is 700 bp. To perform RT-PCR reaction following cycling conditions were used:

| Step | Temperature | Time | No. cycles |
|---|---|---|---|
| Revere transcription | 50° C. | 30 min | 1 |
| RT inactivation/Initial denaturation | 98° C. | 2 min | 1 |
| Amplification | 98° C. | 10 sec | 40 |
| | 65° C. | 10 sec | |
| | 72° C. | 30 sec | |
| Final extension | 72° C. | 1 min | 1 |

After RT-PCR capsules were washed several times with 1× DPBS+0.3% (v/v) NP-40, stained with 1× SYBR Green I and analyzed under fluorescence microscope. To dissolve, the capsules were suspended in 1M alkaline solution incubated at 50° C. for 30 minutes and then neutralized by adding equimolar acetic acid. DNA was extracted and concentrated using 1.8× Agencourt AMPure XP magnetic beads (Beckman Coulter, A63881) and analyzed on 1% agarose gel. Results presented in FIGS. 16-18B unequivocally prove that capsules are applicable in multi-step operations and processes to perform complex biochemical reactions on encapsulated species (e.g. single-cells).

Example 4—Capsules of Different Composition

Using the method and system described here it is possible to generate semi-permeable capsules composed of different polymers. Below we showcase two, but not limited to, examples of PEGDA-Citrate, and PEGDA-PVA capsules.

TABLE 1

PEGDA-Citrate composition

| Volume | Material | Final |
|---|---|---|
| 16.25 μL | 40% (w/w) PEGDA (MW 8K) | 6.5% (w/v) |
| 20 μL | 40% (w/w) Sodium Citrate | 8% (w/v) |
| 2 μL | 5% (w/w) LAP | 0.1% (w/v) |
| 61.75 μL | 1x DBPS | — |
| 100 μL | Final | |

TABLE 2

PEGDA-PVA composition

| Volume | Material | Final |
|---|---|---|
| 10.5 μL | 40% (w/w) PEGDA (MW 6K) | 4.2% (w/v) |
| 65 μL | 10% (w/w) PVA (MW 31-50K) | 6.5% (w/v) |
| 2 μL | 5% (w/w) LAP | 0.1% (w/v) |
| 22.5 μL | 1x DBPS | — |
| 100 μL | Final | |

After combining the reagents as described in Table 1 or Table 2 solutions were mixed well and centrifuge at max speed for 30 minutes. Separate PEGDA and Citrate/PVA phases were loaded onto 20 μm deep co-flow device with the following flow-rates: PEGDA-rich phase—50 μL/h, Citrate/PVA-rich phase—50 μL/h and droplet stabilization oil—350-500 μL/h. After encapsulation initiate the polymerization of ATPS droplets by incubating the tube with emulsion under 365 nm UV lamp for 2.5 minutes or 405 nm laser for 20 seconds. Before releasing capsules, 200-300 μL of 1× DPBS+0.1% Triton X-100 was added on top of emulsion followed by capsule release by adding 200-400 μL of 20% (v/v) PFO. Capsules were washed several times and analysed under the microscope (FIG. 19).

Example 5—Capsules That Are Soluble in Some Reducing Environments

Using the method and system described here it is possible to generate semi-permeable capsules that are sensitive to reducing agents. Below we showcase, but not limited to, an example of capsules whose shell is sensitive to reducing agent. The specific example presented here reveals that by using a cross-linking agent that is sensitive to reducing agent, it is possible to generate stable semi-permeable capsules that can be dissolved in the presence of reducing agent, typically at concentration higher than 1 mM. As referred herein, the reducing agent can be dithiothreitol (DTT), beta-mercaptoehtanol and other compounds of similar nature. To show the example of DTT-soluble capsules, the following reaction mixture was prepared:

| Volume | Component | Final |
|---|---|---|
| 50 μL | 100 mM BAC | 50 mM |
| 7.5 μL | 40% PEGMEMA, 5K | 3% |
| 22 μL | 25% Dextran, 500K | 5.5% |
| 6 μL | 100% PEGMA, 360 | 6% |

-continued

| Volume | Component | Final |
|---|---|---|
| 2.5 µL | 40% APS | 1% |
| 12 µL | 1x DPBS | — |
| 100 µL | Final | |

Note.
BAC—(bis(acryloyl)cystamine); PEGMEMA—poly(ethylene glycol) methyl ether methacrylate; PEGMA—poly (ethylene glycol) methacrylate; APS—ammonium persulfate; DPBS—Dulbecco's phosphate-buffered saline (without calcium and without magnesium).

The reaction mixture was centrifuged at >20.000 RCF for 20 min in order to form two phases—PEG-rich phase and DEX-rich phase. Each phase was loaded into a syringe and injected onto microfluidics chip alongside with droplet stabilization oil containing 1% TEMED. Using 20µm deep co-flow device and the following flow rates: droplet stabilization oil 400 µL/hr, PEG-rich solution—50 µL/hr and 40 µL/hr for DEX-rich solution, approximately 40 µm size ATPS droplets were collected in the form of an emulsion over 1 hour. Emulsion was incubated at 37° C. for 30 minutes to complete hydrogel-shell polymerization. To released hardened capsules the emulsion was broken and capsuled resuspended in 10 mM Tris-HCl with 0.1% Triton X-100 buffer. After several round of washing the capsules were analysed under bright field microscope, showing monodisperse, concentric and nearly-concentric capsules (FIG. 20). To dissolve the capsules, 4 µl of capsule suspension was mixed with 20 µL 10 mM DTT and incubated at room temperature for 10, 30 and 60 mM No capsules were detected after 10 min proving that produced capsules remain intact in aqueous buffers but can be dissolved in the presence of >1 mM DTT.

Example 6—The Use of Capsules, That Are Sensitive to Reducing Agents, in Multi-Step Procedures To prove the suitability of capsules, that are sensitive to reducing agents, in the multi-step procedures biochemical and enzymatic reactions were conducted on encapsulated cells. Following reaction mix was prepared:

| Volume | Component | Final |
|---|---|---|
| 100 µL | 100 mM BAC | 50 mM |
| 15 µL | 40% PEGMEMA, 5K | 3% |
| 44 µL | 25% Dextran, 500K | 5.5% |
| 14 µL | 100% PEGMA, 360 | 7% |
| 5 µL | 40% APS | 1% |
| 22 µL | 1x DPBS | — |
| 200 µL | Final | |

Note.
BAC—(bis(acryloyl)cystamine); PEGMEMA—poly(ethylene glyco) methyl ether methacrylate; PEGMA—poly (ethylene glycol) methacrylate; ammonium persulfate; DPBS—Dulbecco's phosphate-buffered saline (without calcium and without magnesium).

The reaction mixture was centrifuged at >20.000 RCF for 20 mM in order to form two phases—PEG-rich phase and DEX-rich phase. The pellet of E. coli cells was dispersed in DEX-rich phase, loaded into a syringe and injected onto microfluidics chip alongside with PEG-rich phase and droplet stabilization oil containing 1% TEMED. Using 20 µm deep co-flow device and the following flow rates: droplet stabilization oil 400 µL/hr, PEG-rich solution—50 µL/hr and 40 µL/hr for DEX-rich solution containing cells, approximately 40 µm size ATPS droplets were collected in the form of an emulsion over 1 hour. Emulsion was incubated at 37° C. for 30 minutes to complete hydrogel-shell polymerization. To released hardened capsules the emulsion was broken and capsuled resuspended in 10 mM Tris-HCl with 0.05% Triton X-100 buffer. After a few rounds of washing the capsules were analysed under bright field microscope (FIG. 21). The capsules were then suspended in another buffer containing lysis reagents the composition of which is listed below:

| Volume | Component | Final |
|---|---|---|
| 1.5 µL | 33750 U/µL Lysozyme | 50.6 U/µL |
| 10 µL | 10% Triton X-100 | 0.1% |
| 10 µL | 20 mg/mL Proteinase K | 200 µg/mL |
| 100 µL | HBs | — |
| 878.5 µL | 1x TE buffer* | |
| 1000 µL | Final | |

*TE buffer: 10 mM Tris-HCl, 1 mM EDTA, pH 8.

To lyse the cells capsules were incubated in lysis solution at 37° C. for 30 minutes, washed 5-times with 1 mL of 10 mM Tris-HCl containing 0.05% Triton X-100 buffer (using 5000 g/2 min centrifugation). To perform PCR on encapsulated cells following PCR reaction mix was prepared:

| Volume, 1-reaction | Component | Final |
|---|---|---|
| 12.5 µL | 2x KAPA mix | 1x |
| 1 µL | 10 µM Forward primers mix | 0.4 µM |
| 1 µL | 10 µM Reverse primers mix | 0.4 µM |
| 0.5 µL | Water, nuclease-free | — |
| 10 µL | Close-packaged capsules | — |
| 25 µL | Total | |

Note.
kdsC and ompA gene specific primers were used.

After preparing PCR mix samples were incubated in thermo-cycler using following conditions:

| Step | Temp | Time | No Cycles |
|---|---|---|---|
| Initial denaturation | 95° C. | 3 min | 1 |
| Amplification | 98° C. | 20 s | 35 |
| | 60° C. | 15 s | |
| | 72° C. | 40 s/kb | |
| Final extension | 72° C. | 1 min | 1 |
| Hold | 4° C. | ∞ | — |

To visualize the PCR product in capsules, the capsules were washed 3-times with 1 mL Tris-HCl containing 0.05% Triton X-100 and then stained with 1x Syber Green Dye. Results presented in FIG. 21 show the successful PCR reaction in capsules on single-cells.

To release the PCR product from the capsules, 2 µL of closed packed capsules were mixed with 8 µL 10 mM DTT and incubated at room temperature for 30 min. The resulting 10 µL were mixed with 2 µL DNA Loading Dye (6x) and loaded onto agarose gel followed by the electrophoresis. Results presented in FIG. 22 show that PCR product is highly specific, hence unequivocally proving that capsules can withstand multi-step procedures and are suitable to perform complex reactions, and that such capsules can be dissolved at desirable time point by adding certain amount of reducing agent.

We claim:
1. A method of barcoding a nucleic acid population arising from a single cell, comprising encapsulating the single cell in a microcapsule having a semipermeable hydrogel shell and an aqueous interior, lysing the single cell such that the nucleic acid population from the single cell is released into the microcapsule, washing the microcapsule in an aqueous solution comprising a barcode population, and forming phosphodiester bonds between barcodes of the barcode population and nucleic acids of the nucleic acid population in the aqueous interior.

2. The method of claim 1, wherein encapsulating the single cell comprises colocalizing the single cell, a microcapsule aqueous core precursor solution, and a microcapsule semipermeable shell precursor solution in a droplet of a water in oil emulsion comprising an oil carrier; and solidifying the semipermeable shell from the semipermeable shell precursor solution.

3. The method of claim 2, comprising replacing the oil carrier with an aqueous solution.

4. The method of claim 1, comprising, prior to lysing the single cell, suspending the microcapsule in a solution comprising growth medium so as to allow clonal expansion of the single cell to form a cell population comprising the single cell and at least one mitotic sibling of the single cell.

5. The method of claim 1, wherein lysing the single cell comprises resuspending the microcapsule in a lysis solution such that the lysis solution traverses the microcapsule semipermeable shell.

6. The method of claim 5, comprising, subsequent to lysing, resuspending the microcapsule in a wash buffer to remove the lysis solution from the microcapsule.

7. The method of claim 1, comprising, subsequent to lysing, resuspending the microcapsule in a protease solution to clear proteins from the microcapsule.

8. The method of claim 1, comprising, subsequent to lysing, resuspending the microcapsule in a reverse transcription buffer comprising reverse transcriptase to generate cDNA molecules from RNA templates in the nucleic acid population.

9. The method of claim 1, comprising, subsequent to lysing, resuspending the microcapsule in a polymerase buffer comprising a polymerase to amplify at least some of the nucleic acid population.

10. The method of claim 1, wherein the barcode population comprises barcodes that distinguish the microcapsule from nucleic acids of a second microcapsule.

11. The method of claim 1, wherein the barcode population comprises barcodes that are distinct from a second barcode population.

12. The method of claim 1, wherein forming phosphodiester bonds between barcodes of the barcode population and nucleic acids of the nucleic acid population comprises providing the microcapsule with a ligase capable of traversing the semipermeable shell.

13. The method of claim 1, wherein forming phosphodiester bonds between barcodes of the barcode population and nucleic acids of the nucleic acid population comprises providing the microcapsule with a polymerase capable of traversing the semipermeable shell.

14. The method of claim 1, comprising resuspending the microcapsule in a solution comprising sequencing library packaging reagents.

15. The method of claim 1, comprising degrading the semipermeable microcapsule shell.

16. The method of claim 15, wherein the degrading comprises heating.

17. The method of claim 15, wherein the degrading comprises shearing.

18. The method of claim 15, wherein the degrading comprises enzymatic degradation.

19. The method of claim 15, comprising recovering nucleic acids encapsulated in the semipermeable microcapsule shell.

20. The method of claim 19, comprising sequencing at least some of the nucleic acid population.

* * * * *